United States Patent
Holland et al.

(10) Patent No.: US 9,532,993 B2
(45) Date of Patent: Jan. 3, 2017

(54) APREPITANT L-PROLINE SOLVATES—COMPOSITIONS AND COCRYSTALS

(71) Applicant: NUFORMIX LIMITED, Cambridge, Cambridgeshire (GB)

(72) Inventors: Joanne Holland, Cambridge (GB); Christopher Frampton, Stowmarket (GB); Alan Chorlton, Newmarket (GB); Daniel Gooding, Cambridge (GB)

(73) Assignee: NUFORMIX LIMITED (GB)

( * ) Notice: Subject to any disclaimer, the term of this patent is extended or adjusted under 35 U.S.C. 154(b) by 0 days.

(21) Appl. No.: 14/360,071

(22) PCT Filed: Nov. 21, 2012

(86) PCT No.: PCT/IB2012/056590
§ 371 (c)(1),
(2) Date: May 22, 2014

(87) PCT Pub. No.: WO2013/076659
PCT Pub. Date: May 30, 2013

(65) Prior Publication Data
US 2014/0343060 A1 Nov. 20, 2014

Related U.S. Application Data

(60) Provisional application No. 61/563,647, filed on Nov. 25, 2011.

(51) Int. Cl.
| | | |
|---|---|---|
| C07D 413/06 | (2006.01) |
| A61K 31/5377 | (2006.01) |
| A61K 31/401 | (2006.01) |
| C07D 405/06 | (2006.01) |
| A61K 47/10 | (2006.01) |

(52) U.S. Cl.
CPC ......... *A61K 31/5377* (2013.01); *A61K 31/401* (2013.01); *A61K 47/10* (2013.01); *C07D 405/06* (2013.01); *C07D 413/06* (2013.01)

(58) Field of Classification Search
CPC .......................... C07D 413/06; A61K 31/5377
See application file for complete search history.

(56) References Cited

U.S. PATENT DOCUMENTS

| | | | |
|---|---|---|---|
| 5,145,684 | A | 9/1992 | Liversidge et al. |
| 5,719,147 | A | 2/1998 | Dorn et al. |
| 6,048,859 | A | 4/2000 | Dorn et al. |
| 6,096,742 | A | 8/2000 | Crocker et al. |
| 6,235,735 | B1 | 5/2001 | Dorn et al. |
| 9,029,369 | B2 | 5/2015 | Holland et al. |

FOREIGN PATENT DOCUMENTS

| | | |
|---|---|---|
| CN | 1668283 A | 9/2005 |
| JP | 2007524596 A | 8/2007 |
| WO | 95/16679 A1 | 6/1995 |
| WO | 2004/000284 A1 | 12/2003 |
| WO | 2004/078161 A1 | 9/2004 |
| WO | 2004/078163 A3 | 9/2004 |
| WO | 2007/016582 A2 | 2/2007 |
| WO | 2007/147160 A2 | 12/2007 |
| WO | 2009/108828 A2 | 9/2009 |
| WO | 2012/038937 A1 | 3/2012 |

OTHER PUBLICATIONS

Mirza et al. ("Capturing the Advantages of Co-Crystals," Pharmaceutical Technology, v. 22, issue 7, Jul. 1, 2010).*
Schultheiss et al. (Crystal Growth & Design, 2009, v. 9, n. 6, p. 2950-67).*
International Search Report in Application No. PCT/IB2012/056590 dated Mar. 6, 2013.
International Preliminary Report on Patentability in Application No. PCT/IB2012/056590 dated May 27, 2014.
I. Miroshnyk et. al.: "Capturing the Advantages of Co-Crystals," URL: http://license.icopyright.net/user/viewFreeUse.act?fuid=MTQ5MDcwMzA%3D, pp. 1-8, Jul. 1, 2010.
A. Tilborg et. al.: "Advantages of Cocrystallization in the Field of Solid-State Pharmaceutical Chemistry: l-Proline and MnCl2," European Journal of Medicinal Chemistry, vol. 45, No. 8, pp. 3511-3517, Aug. 1, 2010.
Nate Schultheiss et. al.: "Pharmaceutical Cocrystals and Their Physiochemical Properties," Crystal Growth and Design, vol. 9, No. 6, pp. 2950-2967, Jun. 3, 2009.
Search Report and Written Opinion for PCT International Application No. PCT/IB2011/054210, filed Sep. 23, 2011.
Ständer et al., "Targeting the Neurokinin Receptor 1 with Aprepitant: A Novel Antipruritic Strategy," PLoS One 5(6) e10968:1-5 (2010).

(Continued)

*Primary Examiner* — Robert Havlin
(74) *Attorney, Agent, or Firm* — J. A. Lindeman & Co., PLLC

(57) ABSTRACT

Aprepitant L-proline solvate compositions and aprepitant L-proline solvate cocrystals are disclosed as well as pharmaceutical compositions containing them. The compositions and cocrystals of the invention are: 1:1:1 aprepitant L-proline methanol composition; a 1:1:1 aprepitant L-proline methanol cocrystal; a 1:1:1:1 aprepitant L-proline ethanol composition; a 1:1:1 aprepitant L-proline ethanol cocrystal; 1 1:1:1 aprepitant L-proline n-propanol composition; and a 1:1:1 aprepitant L-proline n-propanol cocrystal: The aprepitant L-proline solvate compositions or cocrystals may be used in the same way as aprepitant to treat or prevent disorders relating to emesis, a neuropsychiatric disease, an inflammatory disease, pain, cancer, a skin disease, itch a respiratory disease, or an addiction.

20 Claims, 18 Drawing Sheets

(56) References Cited

OTHER PUBLICATIONS

Munõz et al., "The NK-1 receptor antagonist aprepitant as a broad spectrum antitumor drug" Invest New Drugs 28 (2):187-193 (2010).
Mantyh et al., "Substance P Receptors: Localization by Light Microscopic Autoradiography in Rat Brain Using [3H]SP as the Radioligand," Brain Research 307:147-165 (1987).
Goodman and Gilman's "The Pharmacological Basis of Therapeutics", Tenth Edition, pp. 155-173 (A. Gilman, J. Hardman and L. Limbird, eds., McGraw-Hill Press, 2001).
Remington's Pharmaceutical Sciences, 18th Ed., Table of Contents (Mack Publishing Company, Easton, Pa., 1990).
International Preliminary Report on Patentability for PCT International Application No. PCT/IB2011/054210, filed Sep. 23, 2011.

\* cited by examiner

APREPITANT L-PROLINE SOLVATES—COMPOSITIONS AND COCRYSTALS

CROSS REFERENCE TO RELATED APPLICATIONS

This application claims priority to U.S. application Ser. No. 61/563,647 filed 25 Nov. 2011; the disclosure of which is incorporated herein by reference.

FIELD OF THE INVENTION

The invention relates to a new aprepitant compositions and crystalline compounds containing aprepitant. More particularly, the invention relates to solvated aprepitant L-proline solvate compositions, aprepitant L-proline solvate cocrystals, therapeutic uses of the aprepitant L-proline solvate compositions or cocrystals as well as pharmaceutical compositions containing them.

BACKGROUND

Nausea and vomiting are commonly experienced by cancer patients in the course of their disease and treatment. Nausea and/or vomiting may be a result of the cancer itself or from its treatment. Aprepitant, 2-(R)-(1-(R)-(3,5-bis(trifluoromethyl)-phenyl)ethoxy)-3-(S)-(4-fluoro)-phenyl-4-(3-(5-oxo-1H,4H-1,2,4-triazolo)methylmorpholine, shown below, is a substance P/neurokinin 1 (NK1) receptor antagonist used to prevent of acute and delayed nausea and vomiting associated with moderately- and highly-emetogenic chemotherapy and to prevent postoperative nausea and vomiting (PONV).

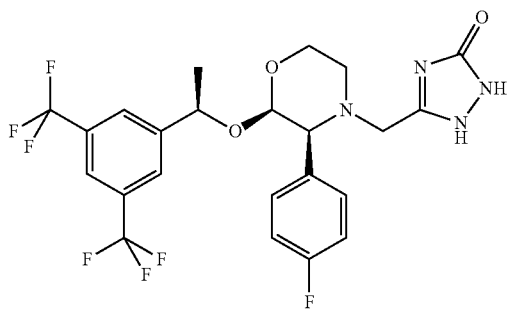 [SMILES: C[C@@H](O[C@H]1OCCN(Cc2nc(=O)[nH][nH]2)[C@H]1c1ccc(F)cc1)c1cc(C(F)(F)F)cc(C(F)(F)F)c1]

The neuropeptide receptors for substance P (neurokinin-1: NK-1) are distributed throughout the mammalian nervous system, the circulatory system and peripheral tissues and are involved in the regulation of a number of biological processes including sensory perception of olefaction, vision, pain, vasodilation, gastric motility and movement control. Substance P antagonists are being studied for their usefulness against neuropsychiatric diseases, inflammatory diseases, pain (including migraine), skin diseases, asthma and other respiratory diseases and emesis. Substance P is known to be a major mediator of pruritus, also commonly known as itch. Studies have reported that aprepitant, as a substance P antagonist, can have a therapeutic effect in the treatment of pruritus (S. Ständer. "Targeting the neurokinin Receptor 1 with aprepitant: a novel antipruritic strategy" *PLoS One.* 2010; 5(6) e10968). The types of itch or skin irritation, include, but are not limited to: a) psoriatic pruritus, itch due to hemodyalisis, aguagenic pruritus, and itching caused by skin disorders (e.g., contact dermatitis), systemic disorders, neuropathy, psychogenic factors or a mixture thereof; b) itch caused by allergic reactions, insect bites, hypersensitivity (e.g., dry skin, acne, eczema, psoriasis), inflammatory conditions or injury; c) itch associated with vulvar vestibulitis; and d) skin irritation or inflammatory effect from administration of another therapeutic such as, for example, antibiotics, antivirals and antihistamines.

It has been demonstrated that NK1 receptors are overexpressed in a wide range of tumor cells and that NK1 receptor antagonists, such as aprepitant, on binding to these receptors can inhibit tumor cell proliferation, angiogenesis and migration of tumor cells. In vitro studies have shown the effectiveness of aprepitant in a range of cancer cell lines including malignant melanoma, neuroblastoma, pancreas, gastric and colon carcinoma cell lines. These studies suggest aprepitant's potential as a broad spectrum anti-tumor drug (M. Muñoz. "The NK-1 receptor antagonist aprepitant as a broad spectrum antitumor drug" *Invest New Drugs.* 2010 April; 28(2): 187-93).

Substance P has been implicated in the response to stress, as well as reward related behaviours (P. W. Mantyh. *Brain Research.* 1987; 307: 147-165). Clinical trials are currently ongoing to investigate whether aprepitant, as a substance P antagonist, could have a positive effect on the cravings and dependency associated with addictive substances such as alcohol, cocaine, opioids, cannabis and tobacco.

Aprepitant is classified by the Biopharmaceutical Classification System (BCS) as a Class IV drug, indicating that it is a low solubility and low permeability API. APIs with poor water solubility are usually characterised by low absorption and poor bioavailability. Aprepitant is a white to off-white crystalline solid which is sparingly soluble in ethanol and isopropyl acetate, slightly soluble in acetonitrile but practically insoluble in water. Aprepitant is identified by CAS Registry Number: 170729-80-3. Aprepitant is disclosed in PCT application WO 95/16679 along with a process for its preparation. See also U.S. Pat. Nos. 5,719,147; 6,048,859; and 6,235,735. U.S. Pat. No. 6,096,742 describes polymorphic forms of aprepitant.

Aprepitant is currently approved for the prevention of nausea and vomiting associated with chemotherapy and also for the prevention of postoperative nausea and vomiting. It is marketed by Merck & Co., Inc, as capsules containing 40 mg, 80 mg and 125 mg of aprepitant for oral administration. Aprepitant was developed and is currently marketed as a nanoparticle formulation to overcome its poor solubility/permeability characteristics. See, e.g., U.S. Pat. No. 5,145,684. But, even with a nanoparticulate formulation, the mean absolute bioavailability of aprepitant is still only 60-65%.

There is a need therefore to develop new forms of aprepitant that have improved dissolution, solubility and/or increased bioavailability. The aprepitant compositions and cocrystals of this invention answer such needs.

PCT application PCT/IB2011/054210, published as WO 028937 A1, describes a 1:1:1 aprepitant L-proline H$_2$O composition and cocrystal. The disclosure of this patent application is incorporated herein by reference.

Although therapeutic efficacy is the primary concern for an active pharmaceutical ingredient (API), the salt and solid state form (i.e., the crystalline or amorphous form) of a drug candidate can be critical to its pharmacological properties, such as bioavailability, and to its development as a viable API. Recently, crystalline forms of API's have been used to alter the physicochemical properties of a particular API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid state properties of the crystalline form of the API, they can significantly impact the selection of a compound as an API, the ultimate pharmaceutical dosage form, the optimization of manufacturing processes, and absorption in the body. Moreover, finding the most adequate solid state form for further drug development can reduce the time and the cost of that development.

Obtaining crystalline forms of an API is extremely useful in drug development. It permits better characterization of the drug candidate's chemical and physical properties. It is also possible to achieve desired properties of a particular API by forming a cocrystai of the API and a coformer Crystalline forms often have better chemical and physical properties than the free base in its amorphous state. Such crystalline forms may, as with the cocrystal of the invention, possess more favorable pharmaceutical and pharmacological properties or be easier to process than known forms of the API itself. For example, a cocrystal may have different dissolution and solubility properties than the API itself and can be used to deliver APIs therapeutically. New drug formulations comprising a cocrystal of a given API may have superior properties over its existing drug formulations. They may also have better storage stability.

Another potentially important solid state property of an API is its dissolution rate in aqueous fluid. The rate of dissolution of an active ingredient in a patient's stomach fluid may have therapeutic consequences since it impacts the rate at which an orally administered active ingredient may reach the patient's bloodstream.

A cocrystal of an API is a distinct chemical composition of the API and coformer(s) and generally possesses distinct crystallographic and spectroscopic properties when compared to those of the API and coformer(s) individually. Crystallographic and spectroscopic properties of crystalline forms are typically measured by X-ray powder diffraction (XRPD) and single crystal X-ray crystallography, among other techniques, Cocrystals often also exhibit distinct thermal behavior. Thermal behavior is measured in the laboratory by such techniques as capillary melting point, thermogravimetric analysis (TGA) and differential scanning calorimetry (DSC).

SUMMARY OF THE INVENTION

The invention relates to a 1:1:1 aprepitant L-proline methanol composition; a 1:1:1 aprepitant L-proline methanol cocrystal; a 1:1:1 aprepitant L-proline ethanol composition; a 1:1:1 aprepitant L-proline ethanol cocrystal; a 1:1:1 aprepitant L-proline n-propanol composition; a 1:1:1 aprepitant L-proline n-propanol cocrystal; as well as pharmaceutical compositions containing these compositions or cocrystals and a pharmaceutically acceptable carrier. The 1:1:1 aprepitant L-proline solvate compositions and cocrystals may be used in the same way as aprepitant to treat or prevent disorders relating to emesis, a neuropsychiatric disease, an inflammatory disease, pain, cancer, a skin disease, itch, a respiratory disease; or an addiction.

DETAILED DESCRIPTION

Figure 1:
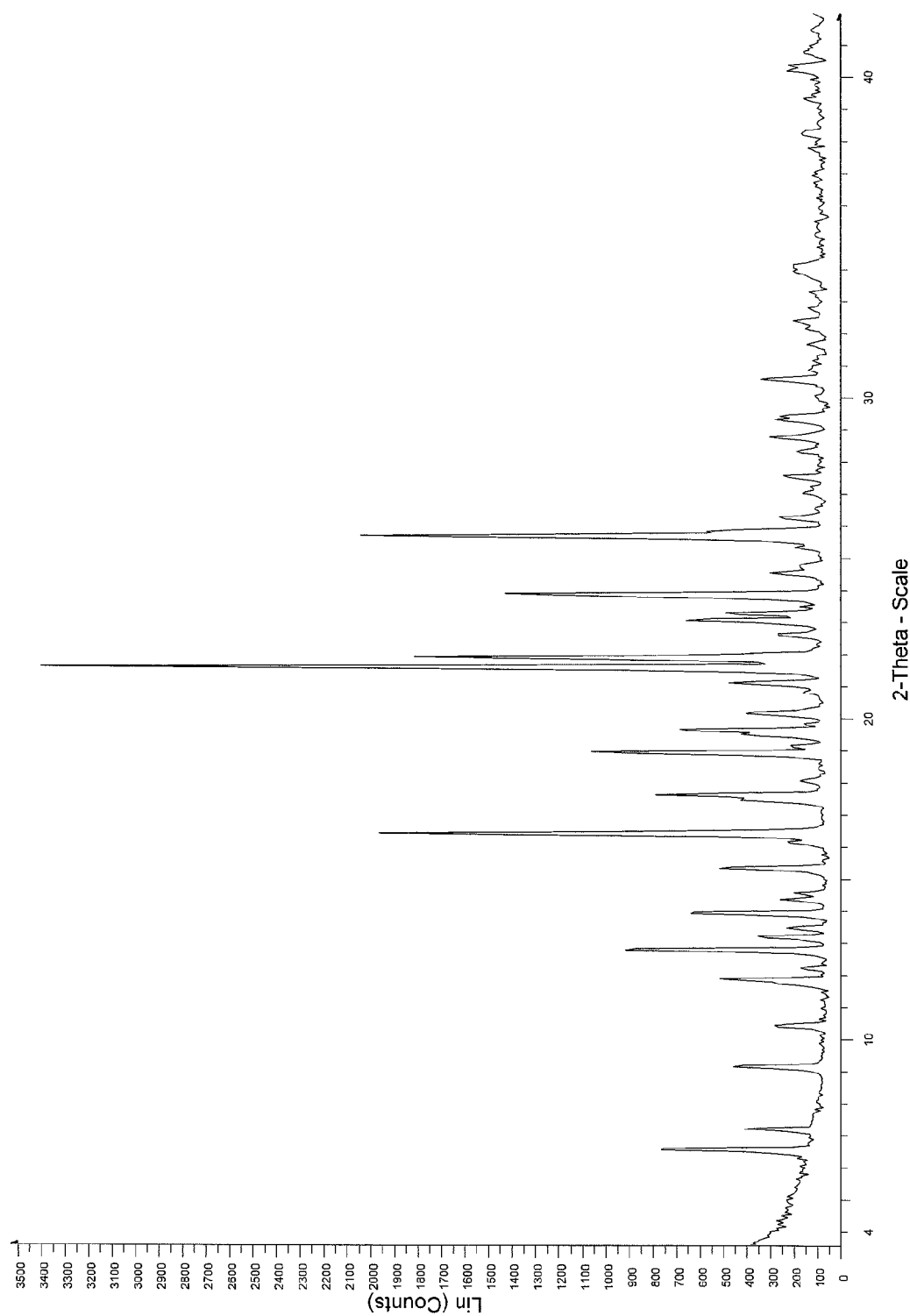
FIG. 1 shows an XRPD pattern of the 1:1:1 aprepitant L-proline MeOH cocrystal.

The invention relates to improvements of the physiochemical and/or the pharmaceutical properties of aprepitant. Disclosed herein are new aprepitant L-proline solvate compositions and cocrystals. The compositions are 1:1:1 aprepitant L-proline solvates where the solvent is methanol (MeOH), ethanol (EtOH), and n-propanol (n-PrOH), and cocrystalline forms of those compositions. More specifically the compositions and cocrystals of the invention are: a 1:1:1 aprepitant L-proline methanol composition; a 1:1:1 aprepitant L-proline methanol cocrystal; a 1:1:1 aprepitant L-proline ethanol composition; a 1:1:1 aprepitant L-proline ethanol cocrystal; a 1:1:1 aprepitant L-proline n-propanol composition; and a 1:1:1 aprepitant L-proline n-propanol cocrystal. The therapeutic uses of the aprepitant L-proline solvate compositions and cocrystals of the invention are described below as well as therapeutic compositions containing them. The cocrystals and the methods used to characterize them are described below.

Though they differ in chemical composition, in their crystalline forms the new 1:1:1 aprepitant L-proline solvate cocrystals of the invention appear isostructual having nearly the same XRPD patterns. The methanol and ethanol cocrystals have virtually identical XRPD patterns. See FIGS. 1, 8 and 15. As shown by the single crystal X-ray characterization, all of the 1:1:1 aprepitant L-proline solvate cocrystals belong to the same space group ($P2_12_12_1$) at 100K. In contrast, the 1:1:1 aprepitant L-proline hydrate is in a different space group at low temperature, 100K, ($P2_1$) but at room temperature, 294 K, exhibits a ($P2_12_12_1$). See PCT Application PCT/IB2011/054210.

Therapeutic Uses of the Aprepitant Composition and Cocrystal

The invention further relates to the therapeutic use of the aprepitant L-proline solvate compositions and cocrystals of the invention to treat or prevent emesis, e.g., vomiting and/or nausea as discussed above. The aprepitant L-proline solvate compositions or cocrystals of the invention may be also used to treat neuropsychiatric diseases, inflammatory diseases, pain (including migraine), cancers, skin diseases, itch, asthma and other respiratory diseases, addiction disorders such as alcoholism, also discussed above. Accordingly, the invention relates to method of treating such a disorder comprising the step of administering to a patient in need thereof a therapeutically effective amount of a 1:1:1 aprepitant L-proline solvate of the invention or of administering to a patient in need thereof a therapeutic composition containing an aprepitant L-proline solvate composition or cocrystal of the invention. The methanol solvate may be used as a therapeutic as the level of methanol actually dosed from the 1:1:1 aprepitant L-proline methanol composition or cocrystal is below the acceptable level for methanol in a therapeutic composition. Of the aprepitant L-proline solvate compositions/cocrystals disclosed here, the n-propanol solvate, 1:1:1 aprepitant L-proline n-PrOH, is generally preferred.

The term "treatment" or "treating" means any treatment of a condition or disorder in a mammal, including: preventing or protecting against the condition or disorder, that is, causing the clinical symptoms not to develop; inhibiting the condition or disorder, that is, arresting or suppressing the development of clinical symptoms; and/or relieving the condition or disorder (including the relief of discomfort associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the condition or disorder. The term "protection" is meant to include "prophylaxis."

Pharmaceutical Compositions Containing the Aprepitant Composition and Cocrystal

The invention also relates to pharmaceutical compositions comprising a therapeutically effective amount of an aprepitant L-proline solvate composition or cocrystal according to the invention and a pharmaceutically acceptable carrier (also known as a pharmaceutically acceptable excipient). As mentioned above, these pharmaceutical compositions are therapeutically useful to treat or prevent disorders, such as those discussed above, relating to emesis, a neuropsychiatric disease, an inflammatory disease, pain, cancer, a skin disease, itch, a respiratory disease, or an addiction.

A pharmaceutical composition of the invention may be in any pharmaceutical form which contains an aprepitant L-proline solvate composition or cocrystal according to the invention. The pharmaceutical composition may be, for example, a tablet, capsule, liquid suspension, injectable, topical, or transdermal. Liquid pharmaceutical compositions may be prepared comprising an aprepitant L-proline solvate of the invention. The pharmaceutical compositions generally contain, for example, about 1% to about 99% by weight of an aprepitant L-proline solvate composition or cocrystal of the invention and, for example, 99% to 1% by weight of at least one suitable pharmaceutical excipient. In one embodiment, the composition may be between about 5% and about 75% by weight of an aprepitant L-proline solvate composition or cocrystal of the invention with the rest being at least one suitable pharmaceutical excipient or at least one other adjuvant, as discussed below.

A "therapeutically effective amount of an aprepitant L-proline solvate composition or cocrystal according to the invention" is that which correlates to about 25 —about 250 mg of aprepitant itself. As discussed above, aprepitant is marketed as 40 mg, 80 mg and 125 mg capsules or a 115 mg injectable by Merck & Co., Inc. under the Emend® tradename. The Emend® product is prescribed to prevent first-day nausea and vomiting related to chemotherapy and continues to prevent delayed nausea that can occur up to 5 days after treatment. Typical doses are about 125 mg 1 hour before chemotherapy on day 1, then 80 mg 1 hour before chemotherapy on days 2 and 3. EMEND® prescribing information.

The actual amount required for treatment of any particular condition or disorder or any particular patient may depend upon a variety of factors including, for example, the disease state being treated and its severity; the specific pharmaceutical composition employed; the age, body weight, general health, sex and diet of the patient; the mode of administration; the time of administration; the route of administration; and the rate of excretion of aprepitant; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, Hardman and L. Limbird, eds., McGraw-Hill Press, 155-173, 2001, which is incorporated herein by reference.

Depending on the type of pharmaceutical composition, the pharmaceutically acceptable carrier may be chosen from any one or a combination of carriers known in the art. The choice of pharmaceutically acceptable carrier depends upon the pharmaceutical form and the desired method of administration to be used. For a pharmaceutical composition of the invention, that is one having an aprepitant L-proline solvate cocrystal of the invention, a carrier may be chosen that maintains the crystalline form. In other words, the carrier should not substantially alter the aprepitant L-proline solvate cocrystal. Nor should the carrier be otherwise incompatible with the aprepitant L-proline solvate composition or cocrystal used, such as by producing any undesirable biological effect or otherwise interacting in a deleterious manner with any other component(s) of the pharmaceutical composition. Once dissolved an aprepitant L-proline solvate composition or cocrystal remains in solution with no re-precipitation of aprepitant, the aprepitant L-proline solvate composition of the invention may therefore be used to prepare liquid formulations of aprepitant.

The pharmaceutical compositions of the invention may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, an aprepitant L-proline solvate composition or cocrystal may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, aliginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents Other formulations suitable for oral administration may be in the form of discrete units as capsules, sachets, or lozenges, in the form of a powder or granules; in the form of a solution or a suspension in an aqueous liquid or non-aqueous liquid, such as ethanol or glycerol; or in the form of an oil-in-water emulsion or a water-in-oil emulsion. A bolus, electuary or paste may also be relevant. Suitable oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents, and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

Compositions for rectal administrations are, for example, suppositories that may be prepared by mixing an aprepitant L-proline solvate composition or cocrystal with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Compositions suitable for topical administration include liquid or semi-liquid preparations such as liniments, lotions, gels, applicants, oil-in-water or water-in-oil emulsions such as creams, ointments, pastes or foams; or solutions or suspensions such as drops, as is known in the art. Composition of the invention intended for topical administration, in which case the carrier may suitably comprise a solution, emulsion, ointment or gel base. The carrier or base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

Because the aprepitant L-proline solvate cocrystalline form may be maintained during preparation, solid dosage forms are preferred for the pharmaceutical composition of the invention. Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier). An aprepitant L-proline solvate composition and cocrystal according to the invention may also be used as to formulate liquid or injectable pharmaceutical compositions. Administration of an aprepitant L-proline $H_2O$ composition or cocrystal in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, intrasystemically, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the condition to be treated.

Aprepitant L-Proline Solvates as Chemical Intermediates

Obtaining a crystalline form of a compound, such as the cocrystals of the invention, is extremely useful in drug development. As discussed above, solid state forms (crystalline or amorphous) of a compound can have different physical and chemical properties, for example, solubility, stability, or the ability to be reproduced. These properties often permit the optimization of manufacturing processes, particularly where a crystalline intermediate is obtained. In multi-step syntheses, such as those described herein, intermediates are prepared and unwanted by-products or impurities can be carried forward from earlier steps. Often filtration, separation, and/or purification steps are introduced to remove unwanted by-products or impurities. Introducing such steps not only can increase manufacturing costs but can also decrease the overall yield of the synthesis. Having a crystalline intermediate within a multistep synthesis can address these problems. A crystalline intermediate provides certain advantages—a high purity intermediate can reduce the need for other purification steps and reduce the cost of the synthetic process.

The aprepitant L-proline solvate cocrystals of the invention are also valuable and useful as high purity chemical intermediates in the preparation other solvates and hydrates. For example, the solvates may be converted to a corresponding solvate by slurrying a cocrystal in the corresponding desired solvent, e.g. the aprepitant L-proline ethanol cocrystal may be converted to the n-PrOH cocrystal by slurrying it in n-propanol or into a hydrate by slurrying it in water or another aqueous solvent system. The 1:1:1 aprepitant L-proline hydrate composition and cocrystal, together with its advantages, are described in PCT Application PCT/IB2011/054210.

EXAMPLES

The following analytical methods were used to characterize the 1:1:1 aprepitant L-proline solvate cocrystals of the invention:

X-Ray Powder Diffraction Characterisation: X-ray powder diffraction patterns for the samples were acquired on a Bruker D8 diffractometer using CuKα radiation (40 kV, 40 mA), θ-2θ goniometer, V4 receiving slits, a Ge monochromator and a Lynxeye detector. The instrument is performance checked using a certified Corundum standard (NIST 1976). The data were collected over an angular range of 2° to 42° 2Θ using a step size of 0.05° 2Θ and a step time of 0.5 seconds. Samples run under ambient conditions were prepared as flat plate specimens using powder as received without grinding. Approximately, 35 mg of the sample was gently packed into a cavity cut into polished, zero background (510) silicon wafer. All samples were analysed using Diffrac Plus EVA v11.0.0.2 or v13.0.0.2.

Single Crystal X-Ray Diffraction (SCXRD): Data were collected on an Oxford Diffraction SuperNova Dual source, Cu at zero, Atlas CCD Diffractometer equipped with an Oxford Cryosystems Cryostream cooling device. Structures were solved using the Bruker SHELXTL program and refined with the SHELXTL program as part of the Bruker SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Thermal Analysis—Differential Scanning Calorimetry (DSC): DSC data was collected on a TA instruments Q2000 equipped with a 50 position autosampler. The calibration for thermal capacity was carried out using sapphire and the calibration for the energy and temperature was carried out using certified indium. Typically 0.8-1.2 mg of each sample, in a pin-holed aluminium pan, was heated at 10° C./min from 25° C. to 350° C. A purge of dry nitrogen at 50 ml/min was maintained over the sample. The instrument control software was Advantage for Q series v2.8.0.392 and Thermal Advantage v4.8.3. All data analysis was performed using Universal Analysis v4.3A software.

Thermo-Gravimetric Analysis (TGA): TGA data were collected on a TA Instruments Q500 TGA, equipped with a 16 position auto-sampler. The instrument was temperature calibrated using certified Alumel. Typically 5-30 mg of each sample was loaded onto a pre-tared platinum crucible and aluminium DSC pan, and was heated at 10° C./min from ambient temperature to 350° C. A nitrogen purge at 60 ml/min was maintained over the sample. The instrument control software was Advantage for Q Series v2.8.0.392 and Thermal Advantage v4.8.3

Solution Proton NMR: $^1$H-NMR spectra were collected using a JEOL EX 270 MHz spectrometer equipped with an auto-sampler. The samples were dissolved in d6-DMSO for analysis. The data was acquired using Delta NMR Processing and Control Software version 4.3.

Gravimetric Vapour Isotherm (GVS) Analysis: Sorption isotherms were obtained using a Hiden Isochema moisture sorption analyser (model IGAsorp), controlled by IGAsorp Systems Software V6.50.48. The sample was maintained at a constant temperature (25° C.) by the instrument controls. The humidity was controlled by mixing streams of dry and wet nitrogen, with a total flow of 250 ml·min$^{-1}$. The instrument was verified for relative humidity content by measuring three calibrated Rotronic salt solutions (10-50-80%). The weight change of the sample was monitored as a function of humidity by a microbalance (accuracy +/−0.005 mg). A defined amount of sample was placed in a tared mesh stainless steel basket under ambient conditions. The sample was loaded at 40% RH and 25° C. (typical room conditions). The sample was initially held at 50% RH for ~80 minutes before the initial desorption cycle was commenced. A moisture sorption isotherm was acquired as outlined in Table 1 (2 scans giving 1 complete cycle). The standard isotherm was collected at a constant temperature (25° C.) and at 10% RH intervals over a 0.5-90% range (80 minutes for each humidity level). Data analysis was undertaken in Microsoft Excel.

TABLE 1

Method Parameters for GVS Experiments

| Parameters | Values |
|---|---|
| Desorption - Scan 1 | 50-0.5 |
| Adsorption/Desorption - Scan 2 & 3 | 0.5-90, 90-0.5 |
| Intervals (% RH) | 10 |
| Number of Scans | 3 |
| Flow rate (ml · min$^{-1}$) | 250 |
| Temperature (° C.) | 25 |
| Stability (° C.min$^{-1}$) | 0.1 |
| Sorption Time (minutes) | 120 minutes time out |

The sample was recovered after completion of the isotherm and re-analysed by XRPD.

Example 1

1:1:1 Aprepitant L-Proline MeOH Cocrystal 1.1 Preparation of a 1:1:1 Aprepitant L-Proline MeOH Cocrystal The batch of the 1:1:1 aprepitant L-proline MeOH cocrystal used for characterisation was prepared as follows:

Aprepitant (300 mg) was weighed into a glass vial. 1.5 ml of a saturated solution of L-proline in methanol was added to the vial. The resulting slurry was placed in a shaker and matured for 5 days (room temperature (RT) to 50° C. on an 8 hour cycle, heating to 50° C. for 4 hours and then cooling to RT for a further 4 hours). The product was then filtered under vacuum and the resulting crystals dried in a vacuum oven at 50° C. overnight.

1.2 XRPD Characterisation of a 1:1:1 Aprepitant L-Proline MeOH Cocrystal

The experimental XRPD pattern of the 1:1:1 aprepitant L-proline MeOH cocrystal is shown in FIG. 1. Table 2 lists the angles, °2θ±0.2°2θ, and d-spacing of the peaks identified in the experimental XRPD pattern of FIG. 1. The entire list of peaks, or a subset thereof, may be sufficient to characterize the cocrystal. For example, this cocrystal may be characterized by a powder x-ray diffraction pattern having at least three or more peaks selected from the peaks at 7.1, 9.1, 10.5, 16.4, 21.6 and 21.9 °2θ±0.2°2θ; as well as by a powder x-ray diffraction pattern substantially similar to FIG. 1

TABLE 2

| Angle °2θ ± 0.2 °2θ | d value Angstrom | Intensity % |
|---|---|---|
| 6.5 | 13.54 | 22.3 |
| 7.1 | 12.36 | 11.8 |
| 9.1 | 9.70 | 13.3 |
| 10.4 | 8.52 | 8.1 |
| 11.8 | 7.47 | 14.9 |
| 12.2 | 7.27 | 4.8 |
| 12.8 | 6.93 | 26.7 |
| 13.2 | 6.72 | 10.1 |
| 13.4 | 6.59 | 6.6 |
| 13.9 | 6.36 | 18.5 |
| 14.3 | 6.18 | 7.4 |
| 15.3 | 5.78 | 14.9 |
| 16.1 | 5.51 | 6.4 |
| 16.4 | 5.41 | 57.6 |
| 17.6 | 5.05 | 22.9 |
| 18.0 | 4.91 | 4.9 |
| 18.9 | 4.68 | 30.9 |
| 19.6 | 4.52 | 19.9 |
| 20.1 | 4.41 | 11.6 |
| 20.8 | 4.27 | 4.5 |
| 21.1 | 4.21 | 13.7 |
| 21.6 | 4.12 | 100.0 |
| 21.9 | 4.06 | 53.2 |
| 22.6 | 3.93 | 7.7 |
| 23.0 | 3.86 | 19.1 |
| 23.2 | 3.83 | 14.1 |
| 23.9 | 3.73 | 41.8 |
| 24.5 | 3.63 | 8.7 |
| 24.8 | 3.59 | 5.0 |
| 25.3 | 3.51 | 5.5 |
| 25.7 | 3.47 | 60.0 |
| 26.2 | 3.40 | 7.5 |
| 27.1 | 3.29 | 4.6 |
| 27.5 | 3.24 | 6.9 |
| 28.3 | 3.15 | 5.4 |
| 28.8 | 3.10 | 8.7 |
| 29.4 | 3.04 | 8.0 |
| 30.6 | 2.92 | 9.8 |
| 31.7 | 2.82 | 4.0 |
| 32.2 | 2.78 | 4.2 |
| 32.4 | 2.76 | 5.8 |
| 34.1 | 2.63 | 5.7 |
| 38.3 | 2.35 | 4.7 |
| 39.4 | 2.29 | 4.5 |
| 40.3 | 2.24 | 5.9 |
| 40.8 | 2.21 | 4.5 |

1.3 SCXRD Characterisation of a 1:1:1 Aprepitant L-Proline MeOH Cocrystal

The crystal used for single crystal structure determination was prepared as follow:

Approximately 20 mg (estimated by eye) of the 1:1:1 aprepitant L-proline MeOH cocrystal batch prepared as previously described was placed in a glass HPLC vial and 1 ml of MeOH was added. The sample was placed on a shaker at 50° C. for ca. 30 minutes before being removed and quickly filtered into a clean glass vial. The vial was covered with film which was then pierced to allow slow evaporation and crystal formation. A suitable single crystal was isolated from the crystals which formed by this method.

Figure 2:
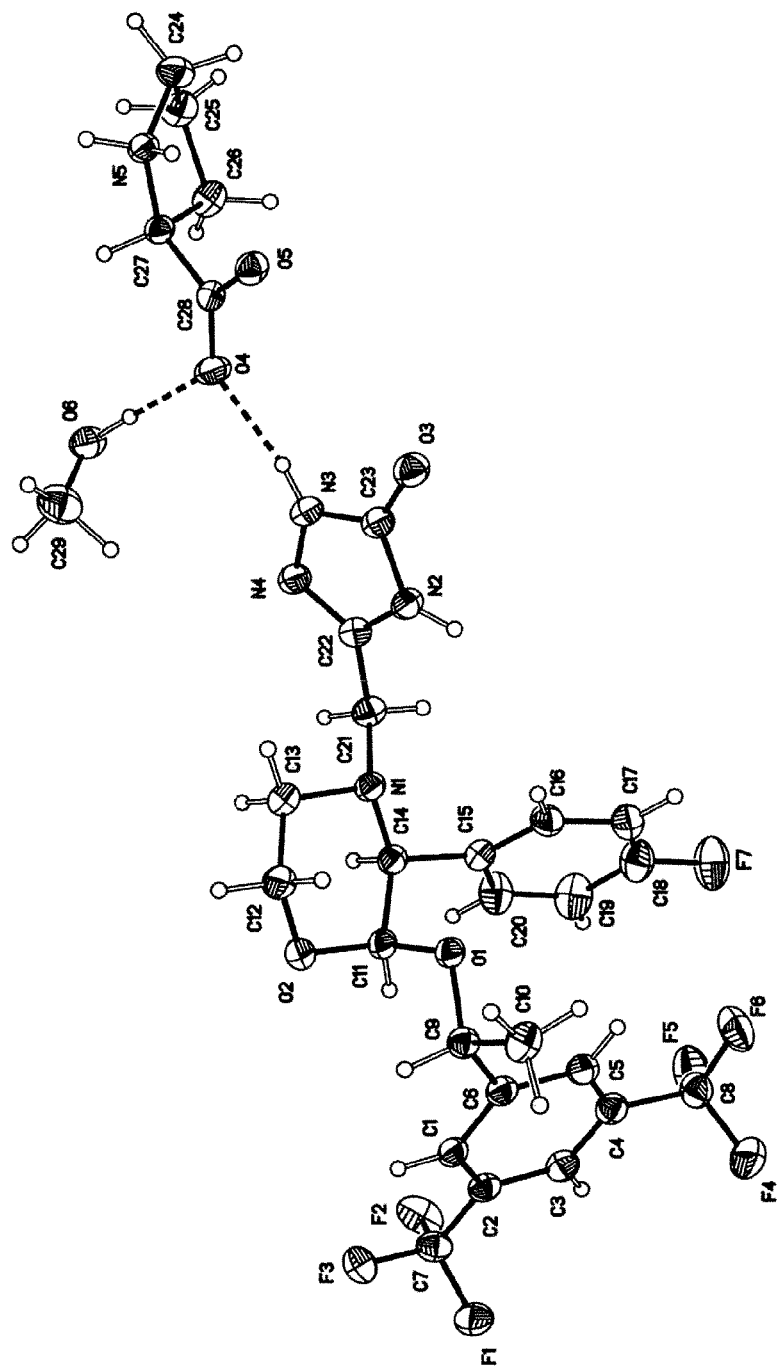
FIG. 2 shows an ORTEP drawing of the 1:1:1 aprepitant L-proline MeOH cocrystal at 100 K.
Figure 3:
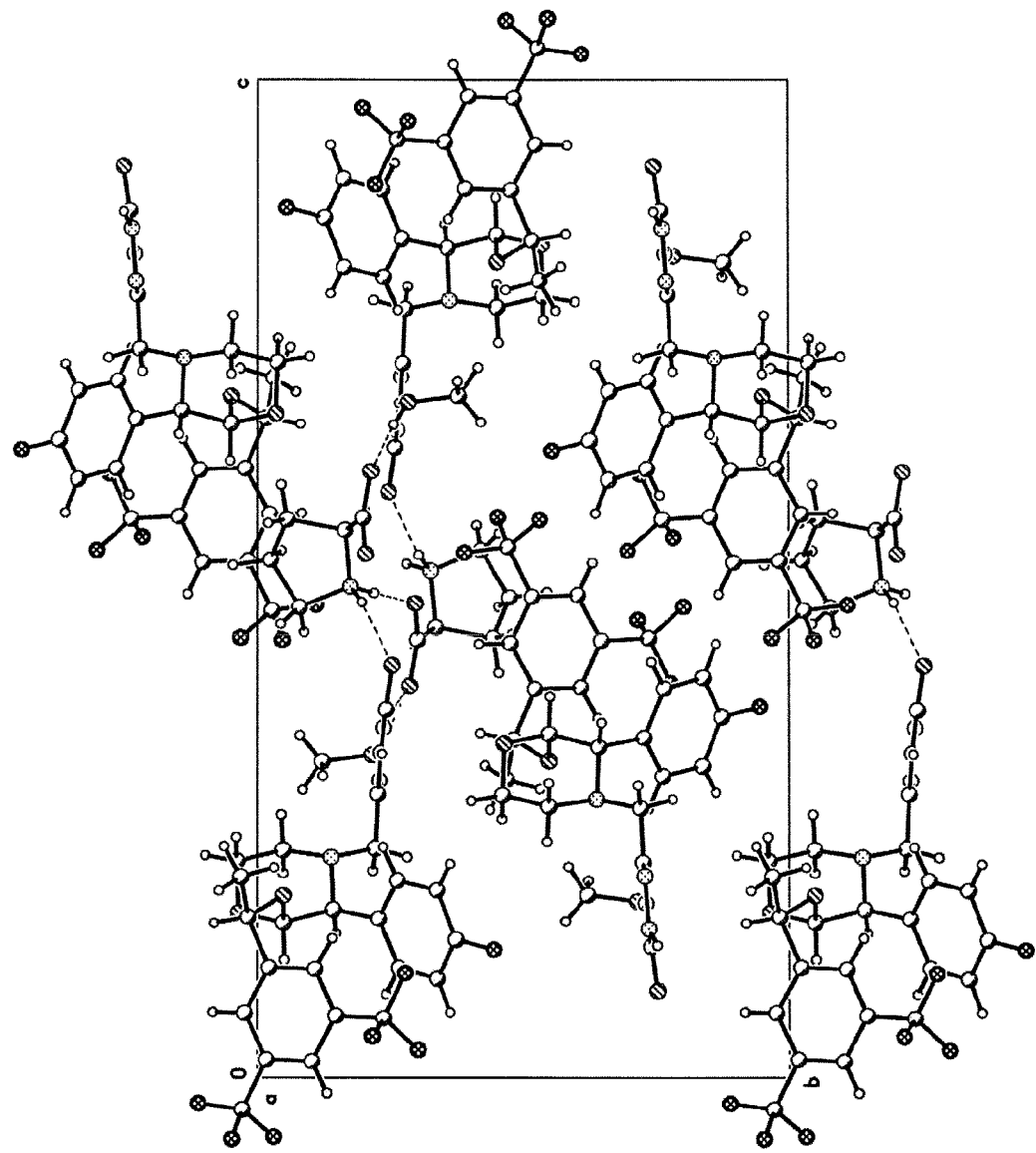
FIG. 3 shows a packing diagram of the 1:1:1 aprepitant L-proline MeOH cocrystal at 100 K.

The single crystal data and structure refinement parameters for the structure measured at 100 K are reported in Table 3. There is a single molecule of the 1:1:1 aprepitant L-proline MeOH cocrystal in the asymmetric unit of the crystal structure. FIG. 2 is an ORTEP diagram of the 1:1:1 aprepitant L-proline MeOH cocrystal showing the numbering scheme employed. Anisotropic atomic displacement ellipsoids for the non-hydrogen atoms are shown at the 50% probability level. Hydrogen atoms are displayed with an arbitrarily small radius. A packing diagram for the 1:1:1 aprepitant L-proline MeOH cocrystal at 100 K with hydrogen bonds shown as dashed lines is shown in FIG. 3. The view is down the a-axis of the unit cell.

Figure 4:
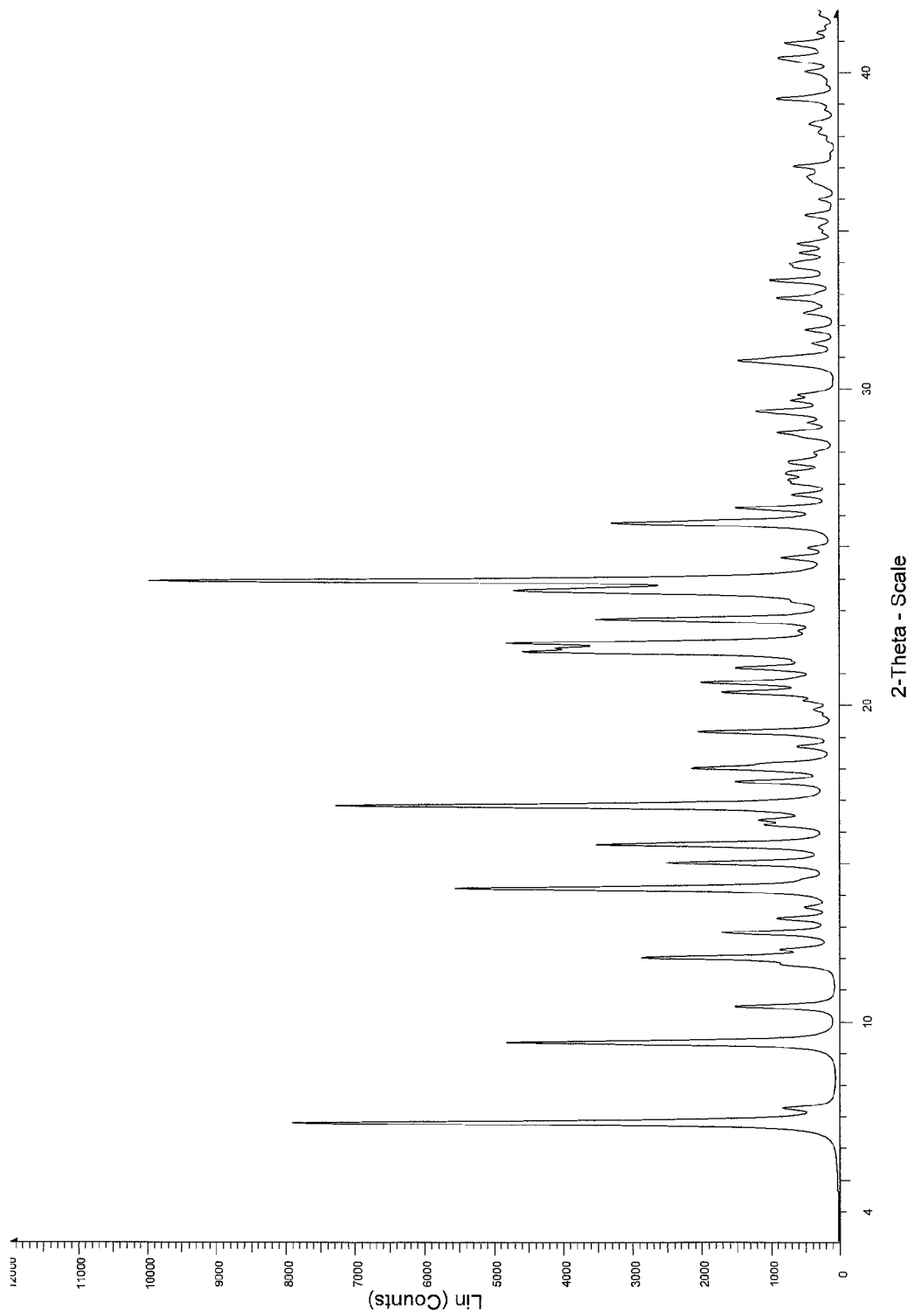
FIG. 4 shows a calculated XRPD pattern for the 1:1:1 aprepitant L-proline MeOH cocrystal at 100 K.

The calculated XRPD pattern based on the single crystal data and structure for the 1:1:1 aprepitant L-proline MeOH cocrystal is shown in FIG. 4. It is also noted that there are some small temperature shifts in some of the peaks owing to the fact that the experimental XRPD pattern was collected at room temperature and the calculated XRPD pattern is derived from data collected at 100 K. There are also small intensity differences owing to preferred orientation effects, present in the experimental pattern.

TABLE 3

| Molecular formula | $C_{29}H_{34}N_5O_6F_7$ |
|---|---|
| Molecular weight | 681.61 |
| Crystal System | Orthorhombic |
| Space Group | $P2_12_12_1$ |
| Unit Cell Dimensions | a = 8.9409(1) Å |
| | b = 13.8361(2) Å |
| | c = 26.1245 (3) Å |
| | α = 90° |
| | β = 90° |
| | γ = 90° |
| Cell Volume | V = 3231.79(7) Å$^3$ |
| Z | 4 |
| Temperature | 100(1) K |
| Radiation Wavelength/type | 1.54178/CuKα |
| Number of Reflections collected | 17826 |
| Number of unique reflections | 6765 |
| $R_{int}$ | 0.0286 |
| Number of observed Reflections, (I > 2σ(I)) | 6135 |
| Resolution, Max. 2θ, Completeness | 0.80 Å, 149.0°, 99.4% |
| wR$^2$ (all data) | 0.0958 |
| $R_1$ (I > 2σ(I)) | 0.0352 |
| Goodness of Fit | 1.006 |
| Flack parameter | −0.02(8) |
| Residual density (Max. Min.), eÅ$^{-3}$ | 0.338, −0.215 |
| Morphology | Colourless Lath |

1.4 DSC of the 1:1:1 Aprepitant L-Proline MeOH Cocrystal

Figure 5:
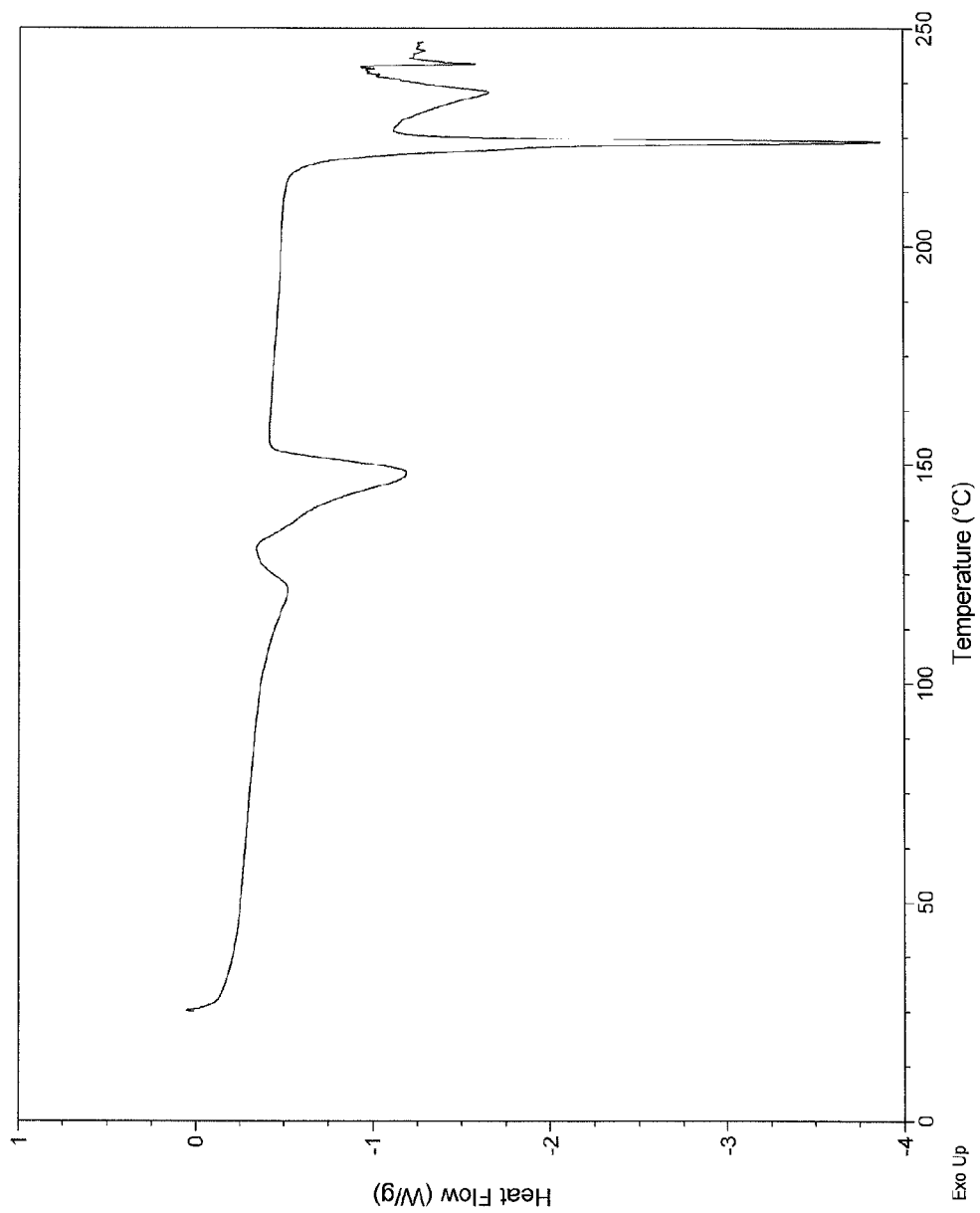
FIG. 5 shows a DSC trace for the 1:1:1 aprepitant L-proline MeOH cocrystal.

The differential scanning calorimetry (DSC) trace obtained for the 1:1:1 aprepitant L-proline MeOH cocrystal is shown in FIG. 5. Two broad endotherms are observed over the temperature ranges 95-130° C. and 130-155° C. These are followed by an endotherm with an onset temperature of 222.1° C. and a peak maximum of 223.9° C.

1.4 TGA of the 1:1:1 Aprepitant L-Proline MeOH Cocrystal

Figure 6:
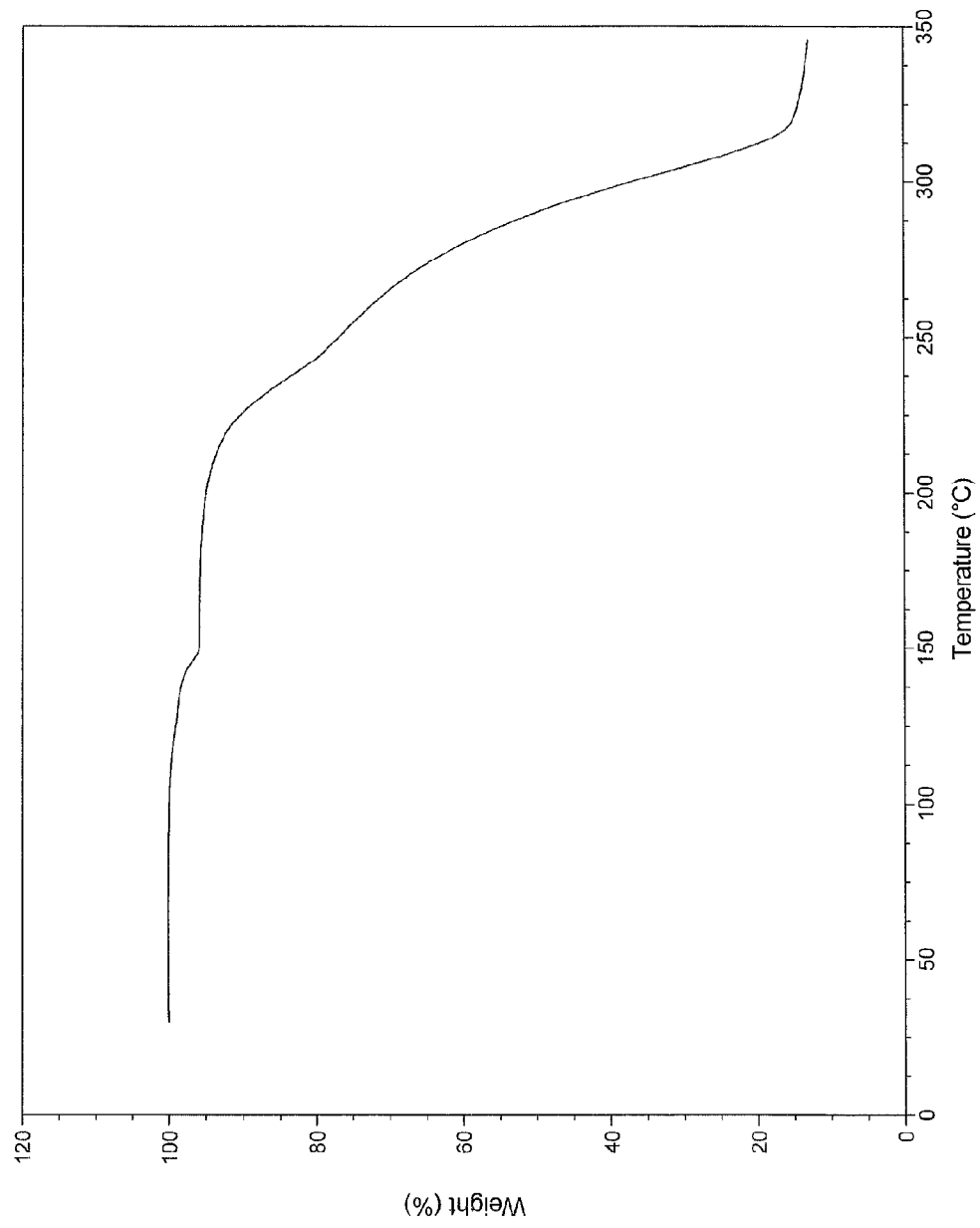
FIG. 6 shows a TGA trace for the 1:1:1 aprepitant L-proline MeOH cocrystal.

In the thermal gravimetric analysis (TGA) trace, FIG. 6, it can be seen that there is negligible weight loss before 100° C. (with 99.9% weight remaining at 100° C.). Over the temperature range 100-190° C. there is a weight loss of 4.7% which corresponds to the loss of one mole of methanol.

1.5 $^1$H NMR Spectrum of the 1:1:1 Aprepitant L-Proline MeOH Cocrystal

Figure 7:
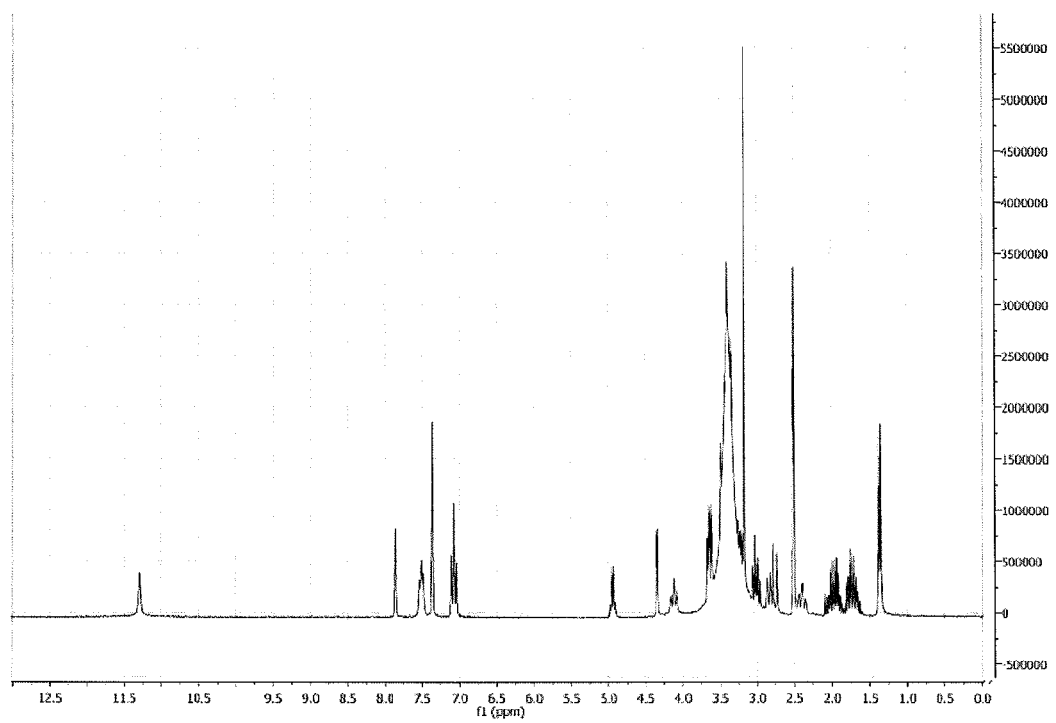
FIG. 7 shows the $^1$H NMR spectrum of 1:1:1 aprepitant L-proline MeOH cocrystal.

The $^1$H NMR spectrum of the 1:1:1 aprepitant L-proline MeOH cocrystal, shown in FIG. 7, displays the following peaks: $^1$H NMR (400 MHz, d6-DMSO) δ: 11.29 (1H), 7.85 (1H), 7.51 (2H), 7.37 (2H), 7.08 (2H), 4.94 (1H), 4.34 (1H), 4.12 (1H), 3.65 (1H), 3.50 (1H), 3.34 (1H), 3.22 (1H), 3.17 (3H), 3.01 (1H), 2.85 (1H), 2.76 (1H), 2.40 (1H), 1.98 (2H), 1.75 (2H) and 1.36 (3H). The peak at 1.97 ppm in the $^1$H NMR spectrum corresponds to two protons on the pyrrolidine ring of L-proline. Comparison of the integration of this peak with that at 7.86 ppm, which corresponds to one of the aromatic protons of aprepitant, indicates that the cocrystal has an aprepitant:L-proline stoichiometry of 1:1.

Figure 8:
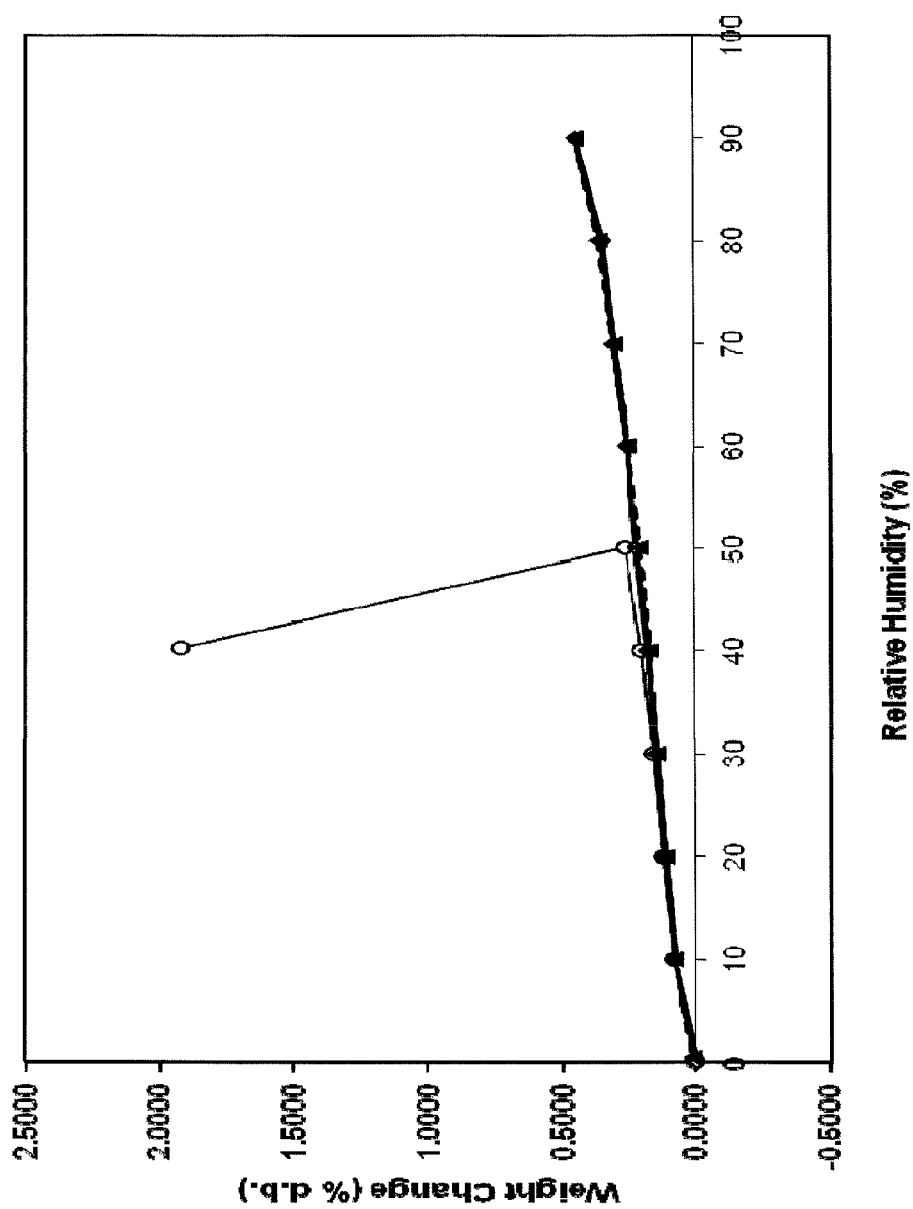
FIG. 8 shows the GVS isotherm graph for the 1:1:1 aprepitant L-proline MeOH cocrystal.

1.6 Gravimetric Vapour Sorption (GVS) Analysis of the 1:1:1 Aprepitant L-Proline MeOH Cocrystal The moisture sorption isotherm graph obtained for the 1:1:1 aprepitant L-proline MeOH cocrystal is shown in FIG. 8. A sample size of 13.8 mg was used for the analysis. It can be seen that during the initial desorption cycle a weight loss of 1.9% occurs. The obtained product was not hygroscopic, only adsorbing 0.4% water at high relative humidity, XRPD analysis of the product obtained after the GVS analysis confirmed that this was entirely the 1:1:1 aprepitant L-proline H$_2$O cocrystal previously described in PCT application PCT/IB2011/054210. The 1.9% weight loss corresponds to the complete conversion of the 1:1:1 aprepitant L-proline MeOH cocrystal into the 1:1:1 aprepitant L-proline H$_2$O cocrystal.

Example 2

1:1:1 Aprepitant L-proline EtOH Cocrystal 2.1 Preparation of a 1:1:1 Aprepitant L-Proline EtOH Cocrystal The batch of the 1:1:1 aprepitant L-proline EtOH cocrystal used for characterisation was prepared as follows:

Aprepitant (300 mg) and L-proline (64.6 mg) were weighed into a glass vial. Ethanol (1.5 ml) was added to the vial. The resulting slurry was placed in a shaker and matured for 5 days (RT to 50° C. on an 8 hour cycle, heating to 50° C. for 4 hours and then cooling to RT for a further 4 hours). The product was then filtered under vacuum and the resulting crystals dried in a vacuum oven at 50° C. overnight.

2.2 XRPD Characterisation of a 1:1:1 Aprepitant L-Proline EtOH Cocrystal

Figure 9:
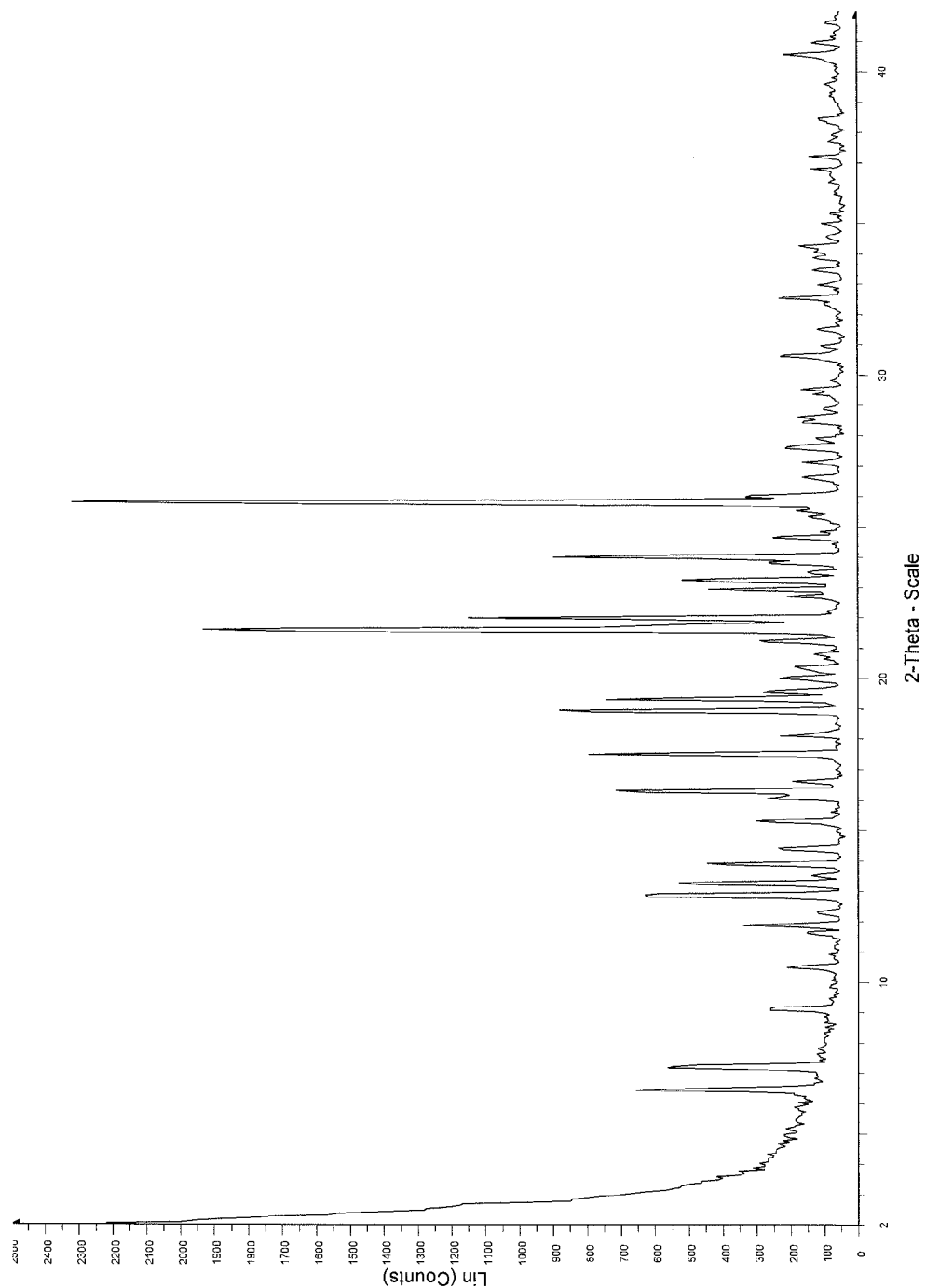
FIG. 9 shows an XRPD pattern for the 1:1:1 aprepitant L-proline EtOH cocrystal.

The experimental XRPD pattern of the 1:1:1 aprepitant L-proline EtOH cocrystal is shown in FIG. 9. Table 4 lists the angles, °2θ±0.2°2θ, and d-spacing of the peaks identified in the experimental XRPD pattern of FIG. 9. The entire list of peaks, or a subset thereof, may be sufficient to characterize the cocrystal. For example, this cocrystal may be characterized by a powder x-ray diffraction pattern having at least three peaks selected from the peaks at 7.2, 9.1, 10.4, 16.2, 21.6 and 22.0 °2θ±0.2°2θ; as well as by a powder x-ray diffraction pattern substantially similar to FIG. 9.

TABLE 4

| Angle °2θ ± 0.2 °2θ | d value Angstrom | Intensity % |
|---|---|---|
| 6.4 | 13.81 | 28.0 |
| 7.2 | 12.32 | 24.1 |
| 9.1 | 9.73 | 11.0 |
| 10.4 | 8.46 | 8.8 |
| 11.6 | 7.63 | 6.4 |
| 11.9 | 7.46 | 14.4 |
| 12.2 | 7.23 | 5.0 |
| 12.8 | 6.89 | 26.9 |
| 13.2 | 6.69 | 22.5 |
| 13.5 | 6.54 | 5.7 |
| 13.8 | 6.40 | 18.9 |
| 14.3 | 6.17 | 9.9 |
| 15.3 | 5.80 | 12.8 |
| 16.0 | 5.52 | 11.3 |
| 16.2 | 5.45 | 30.5 |
| 16.6 | 5.35 | 8.1 |
| 17.5 | 5.06 | 34.1 |
| 18.1 | 4.90 | 9.7 |
| 18.9 | 4.69 | 37.8 |
| 19.3 | 4.59 | 31.9 |
| 19.5 | 4.54 | 11.8 |
| 20.0 | 4.44 | 9.7 |
| 20.3 | 4.36 | 7.9 |
| 20.7 | 4.28 | 5.4 |
| 21.2 | 4.19 | 12.2 |
| 21.6 | 4.11 | 83.2 |
| 22.0 | 4.04 | 49.4 |
| 22.7 | 3.91 | 8.7 |
| 22.9 | 3.88 | 18.7 |
| 23.2 | 3.83 | 22.2 |
| 23.5 | 3.78 | 6.1 |
| 24.0 | 3.70 | 38.5 |
| 24.7 | 3.61 | 10.6 |
| 25.3 | 3.51 | 6.0 |
| 25.8 | 3.45 | 100.0 |
| 26.6 | 3.35 | 6.7 |
| 27.1 | 3.29 | 6.7 |
| 27.6 | 3.23 | 8.9 |
| 27.9 | 3.19 | 5.0 |
| 28.5 | 3.13 | 6.5 |
| 29.5 | 3.02 | 6.9 |
| 30.6 | 2.92 | 9.5 |
| 32.6 | 2.75 | 9.7 |
| 33.5 | 2.67 | 5.5 |
| 33.9 | 2.64 | 5.3 |
| 34.2 | 2.62 | 7.1 |
| 36.8 | 2.44 | 5.6 |
| 37.2 | 2.42 | 5.8 |
| 40.5 | 2.22 | 9.0 |
| 41.0 | 2.20 | 5.5 |

2.3 DSC of the 1:1:1 Aprepitant L-Proline EtOH Cocrystal

Figure 10:
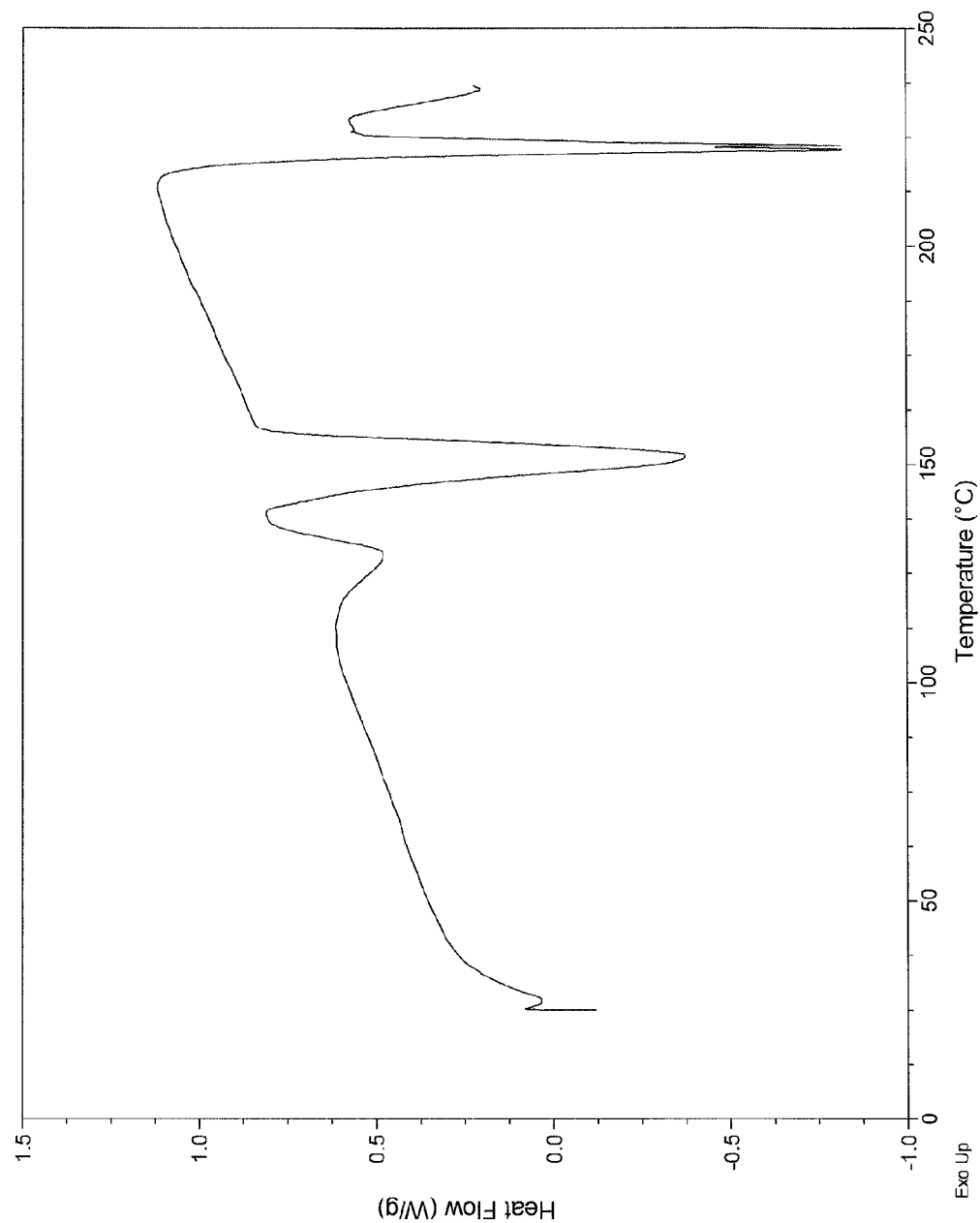
FIG. 10 shows a DSC trace for the 1:1:1 aprepitant L-proline EtOH cocrystal.

The differential scanning calorimetry (DSC) trace obtained for the 1:1:1 aprepitant L-proline EtOH cocrystal is shown in FIG. 10. It can be seen that there are two broad endotherms over the temperature ranges 112-138° C. and 138-159° C. followed by a double endotherm with an onset temperature of 220.0° C. and peak maximums of 222.1° C. and 223.1° C.

2.4 TGA of the 1:1:1 Aprepitant L-Proline EtOH Cocrystal

Figure 11:
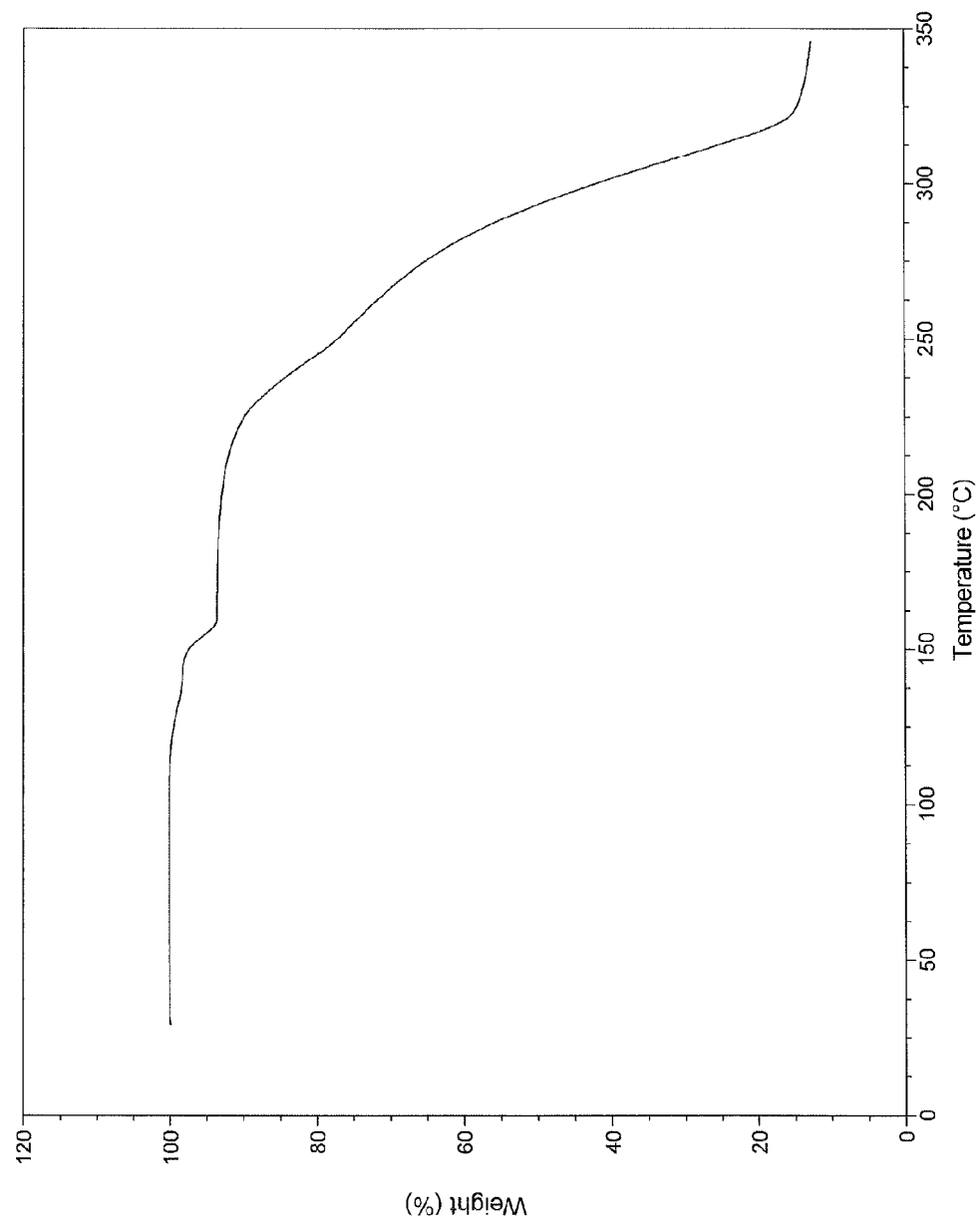
FIG. 11 shows a TGA trace for the 1:1:1 aprepitant L-proline EtOH cocrystal.

In the thermal gravimetric analysis (TGA) trace, FIG. 11, it can be seen that there is negligible weight loss before 110° C. (with 100% weight remaining at 110° C.). Over the temperature range 110-180° C. there is a weight loss of 6.6% which corresponds to 1 mole of ethanol.

2.5 $^1$H NMR Spectrum of the 1:1:1 Aprepitant L-Proline EtOH Cocrystal

Figure 12:
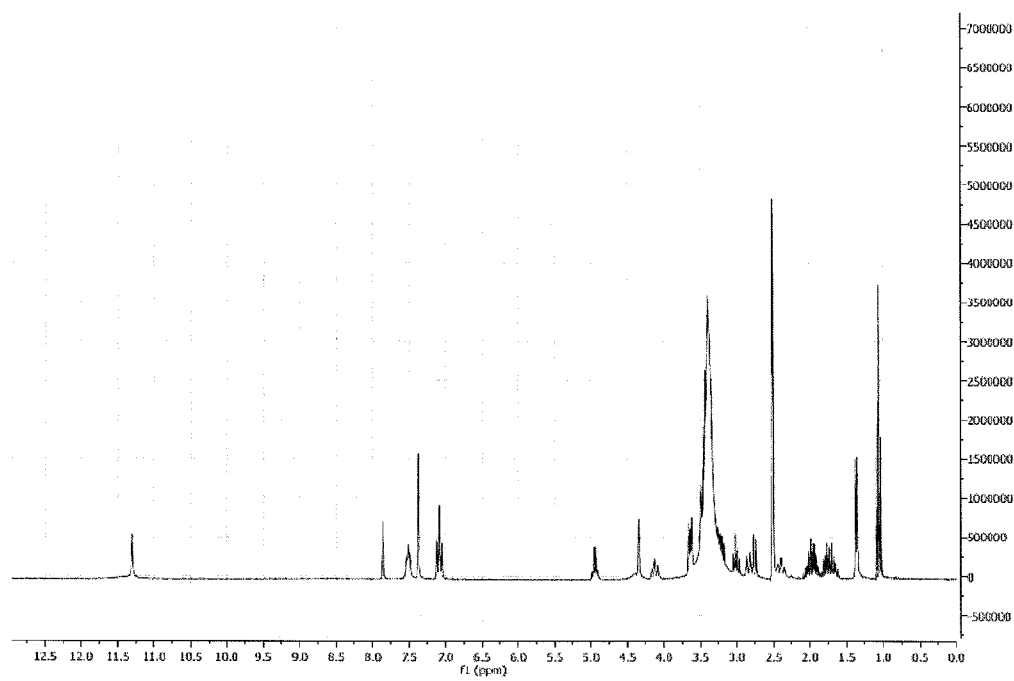
FIG. 12 shows the $^1$H NMR spectrum of the 1:1:1 aprepitant L-proline EtOH cocrystal.

The $^1$H NMR spectrum of the 1:1:1 aprepitant L-proline EtOH cocrystal, shown in FIG. 12, displays the following peaks: $^1$H NMR (400 MHz, d6-DMSO) δ: 11.30 (1H), 7.86 (1H), 7.51 (2H), 7.37 (2H), 7.08 (2H), 4.95 (1H), 4.39 (1H), 4.34 (1H), 4.12 (1H), 3.64 (1H), 3.49 (1H), 3.44 (2H), 3.34 (1H), 3.22 (1H), 3.00 (1H), 2.84 (1H), 2.76 (1H), 2.40 (1H), 1.97 (2H), 1.73 (2H), 1.37 (3H) and 1.06 (3H). The peak at 1.97 ppm in the $^1$H NMR spectrum corresponds to two protons on the pyrrolidine ring of proline. Comparison of the integration of this peak with that at 7.86 ppm, which corresponds to one of the aromatic protons of aprepitant, indicates that the cocrystal has an aprepitant:L-proline stoichiometry of 1:1.

Figure 13:
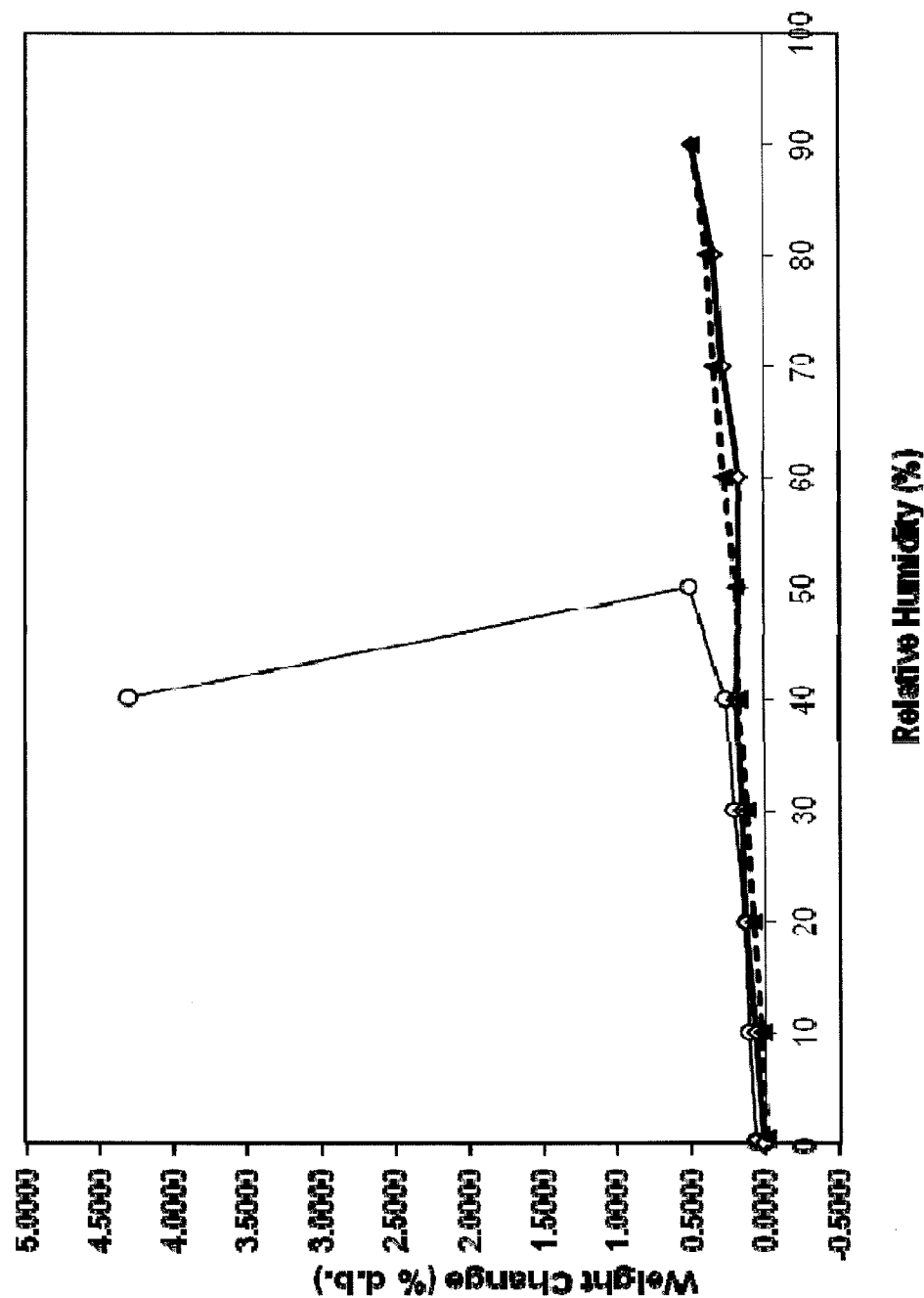
FIG. 13 shows the GVS isotherm graph for the 1:1:1 aprepitant L-proline EtOH cocrystal.

2.6 Gravimetric Vapour Sorption (GVS) Analysis of the 1:1:1 Aprepitant L-Proline EtOH Cocrystal The moisture sorption isotherm graph obtained for the 1:1:1 aprepitant L-proline EtOH cocrystal is shown in FIG. 13. A sample size of 8.8 mg was used for the analysis. It can be seen that during the initial desorption cycle a weight loss of 4.3% occurs. The obtained product was not hygroscopic, only adsorbing 0.5% water at high relative humidity. XRPD analysis of the product obtained after the GVS analysis confirmed that this was entirely the 1:1:1 aprepitant L-proline $H_2O$ cocrystal. A weight loss of 4.3% is equivalent to the complete conversion of the 1:1:1 aprepitant L-proline EtOH cocrystal into the 1:1:1 aprepitant L-proline $H_2O$ cocrystal.

Example 3

1:1:1 Aprepitant L-Proline n-PrOH Cocrystal 3.1 Preparation of a 1:1:1 Aprepitant L-Proline n-PrOH Cocrystal The batch of the 1:1:1 aprepitant L-proline n-PrOH cocrystal used for characterisation was prepared as follows:

Aprepitant (300 mg) and L-proline (64.6 mg) were weighed into a glass vial. n-Propanol (1.5 ml) was added to the vial. The resulting slurry was placed in a shaker and matured for 5 days (RT to 50° C. on an 8 hour cycle, heating to 50° C. for 4 hours and then cooling to RT for a further 4 hours). The product was then filtered under vacuum and the resulting crystals dried in a vacuum oven at 50° C. overnight.

3.2 XRPD Characterisation of a 1:1:1 Aprepitant L-Proline n-PrOH Cocrystal

Figure 14:
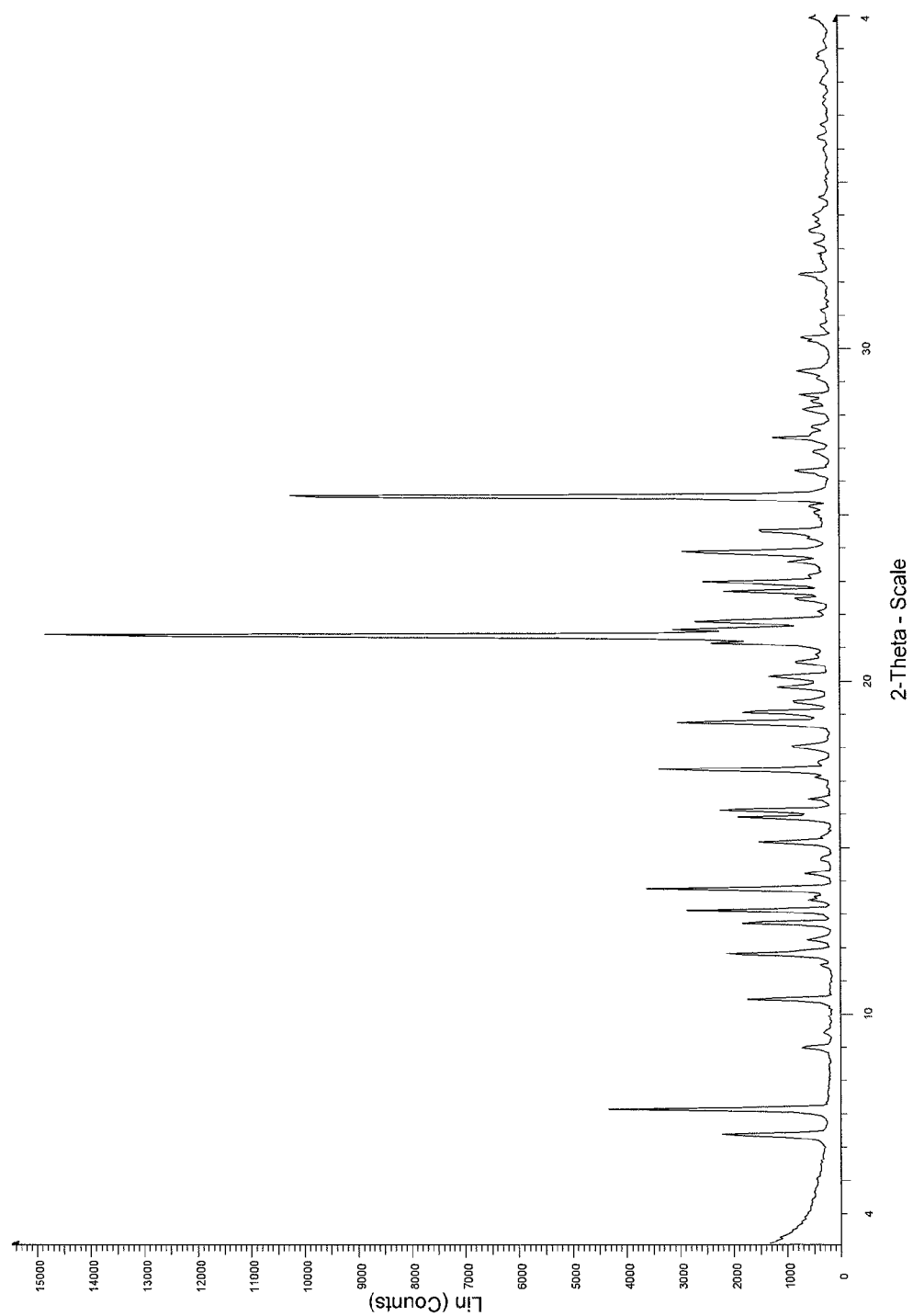
FIG. 14 shows an XRPD pattern for the 1:1:1 aprepitant L-proline n-PrOH cocrystal.

The experimental XRPD pattern of the 1:1:1 aprepitant L-proline n-PrOH cocrystal is shown in FIG. 14. Table 5 lists the angles, °2θ±0.2°2θ, and d-spacing of the peaks identified in the experimental XRPD pattern of FIG. 14. The entire list of peaks, or a subset thereof, may be sufficient to characterize the cocrystal. For example, this cocrystal may be characterized by a powder x-ray diffraction pattern having at least three peaks selected from the peaks at 6.3, 7.1, 9.0, 10.4, 13.7 and 17.3 °2θ±0.2°2θ; as well as a powder x-ray diffraction pattern substantially similar to FIG. 14. It should be noted that the diffractogram of this batch of material also contains peaks at 9.4, 14.6, 18.0, 19.4 and 20.6 °2θ which may be characteristic of the 1:1:1 apreoitant L-proline hydrate cocrystal previously described in PCT application PCT/IB2011/054210, indicating the possible presence of traces of the 1:1:1 aprepitant L-proline hydrate cocrystal as a physical impurity.

TABLE 5

| Angle °2θ ± 0.2 °2θ | d value Angstrom | Intensity % |
|---|---|---|
| 6.3 | 13.91 | 14.7 |
| 7.1 | 12.47 | 29.1 |
| 9.0 | 9.86 | 4.7 |
| 10.4 | 8.49 | 11.5 |
| 11.8 | 7.53 | 14.1 |
| 12.2 | 7.24 | 3.9 |
| 12.7 | 6.96 | 12.2 |
| 13.1 | 6.77 | 19.1 |
| 13.4 | 6.60 | 3.8 |
| 13.7 | 6.44 | 24.2 |
| 14.2 | 6.24 | 4.2 |
| 15.1 | 5.85 | 10.1 |
| 15.9 | 5.57 | 12.7 |
| 16.1 | 5.50 | 14.9 |
| 16.4 | 5.39 | 3.7 |
| 17.3 | 5.13 | 22.7 |
| 18.7 | 4.73 | 20.2 |
| 19.1 | 4.66 | 12.0 |
| 19.3 | 4.59 | 5.6 |
| 19.8 | 4.47 | 7.6 |
| 20.1 | 4.42 | 8.7 |
| 21.4 | 4.15 | 100.0 |
| 21.8 | 4.08 | 18.0 |
| 22.5 | 3.95 | 5.4 |
| 22.7 | 3.92 | 14.3 |
| 22.9 | 3.88 | 17.0 |
| 23.6 | 3.77 | 6.2 |
| 23.8 | 3.73 | 19.5 |
| 24.5 | 3.63 | 9.9 |
| 25.6 | 3.48 | 69.0 |
| 26.3 | 3.38 | 5.3 |
| 27.3 | 3.26 | 8.1 |
| 28.1 | 3.17 | 4.3 |
| 28.6 | 3.12 | 4.7 |
| 29.3 | 3.04 | 5.0 |
| 30.3 | 2.95 | 4.5 |
| 32.3 | 2.77 | 4.7 |

3.3 SCXRD Characterisation of a 1:1:1 Aprepitant L-Proline n-PrOH Cocrystal

A suitable single crystal chosen from the batch of the 1:1:1 aprepitant L-proline n-PrOH cocrystal used for characterisation, prepared as described above, was analysed by single crystal x-ray diffraction.

Figure 15:
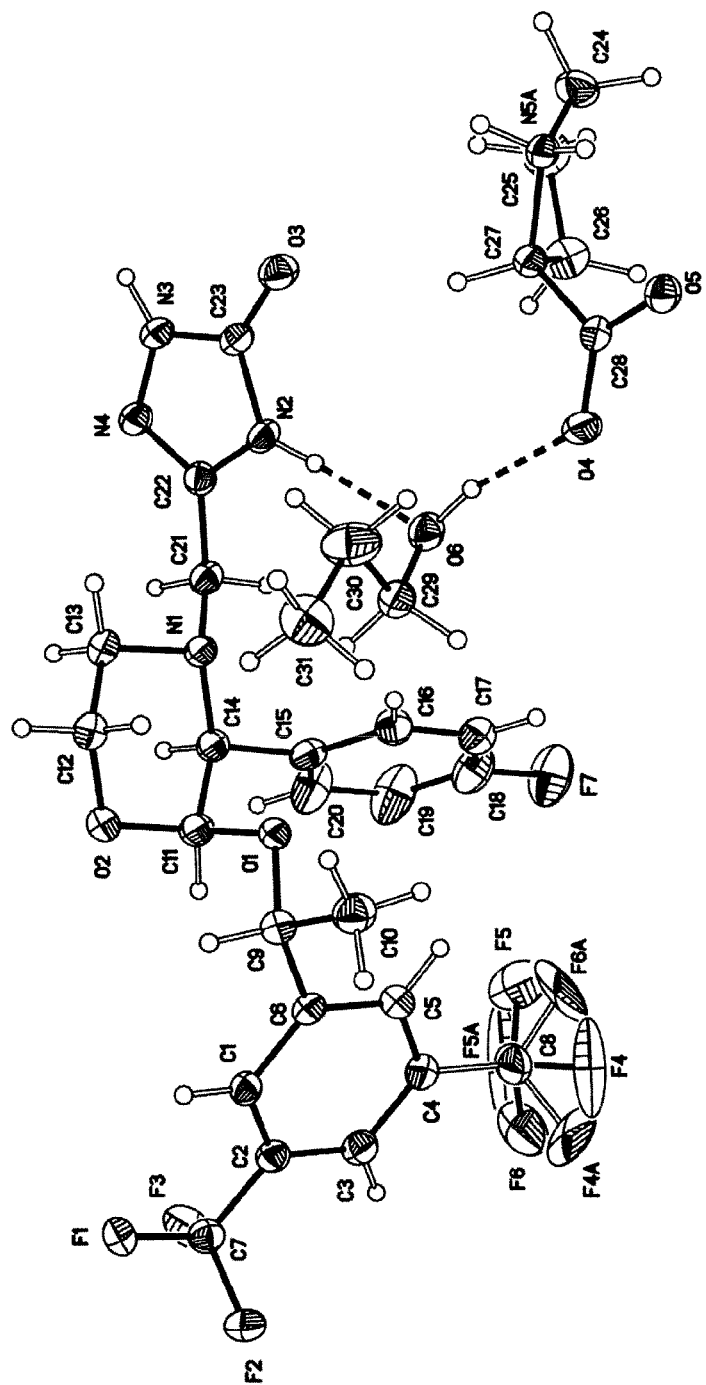
FIG. 15 shows an ORTEP drawing of the 1:1:1 aprepitant L-proline n-PrOH cocrystal at 100 K.
Figure 16:
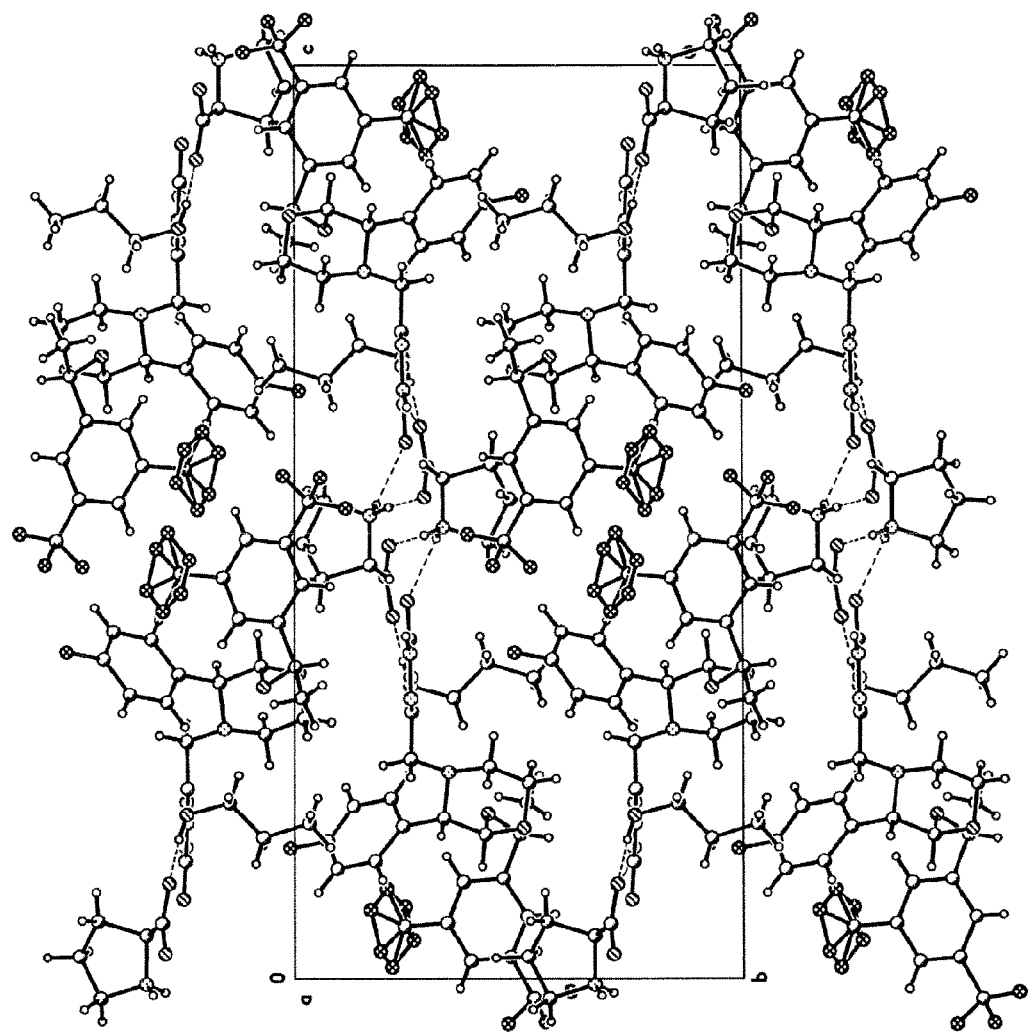
FIG. 16 shows a packing diagram of the 1:1:1 aprepitant L-proline n-PrOH cocrystal at 100 K.

The single crystal data and structure refinement parameters for the structure measured at 100 K are reported in Table 6. There is a single molecule of the 1:1:1 aprepitant L-proline PrOH cocrystal in the asymmetric unit of the crystal structure. One —$CF_3$ group shows significant rotational disorder and was refined with a 2 part model. FIG. 15 is an ORTEP diagram of the 1:1:1 aprepitant L-proline n-PrOH cocrystal showing the numbering scheme employed. Anisotropic atomic displacement ellipsoids for the non-hydrogen atoms are shown at the 50% probability level. Hydrogen atoms are displayed with an arbitrarily small radius. A packing diagram for the 1:1:1 aprepitant L-proline n-PrOH cocrystal at 100 K with hydrogen bonds shown as dashed lines is shown in FIG. 16. The view is down the a-axis of the unit cell.

Figure 17:
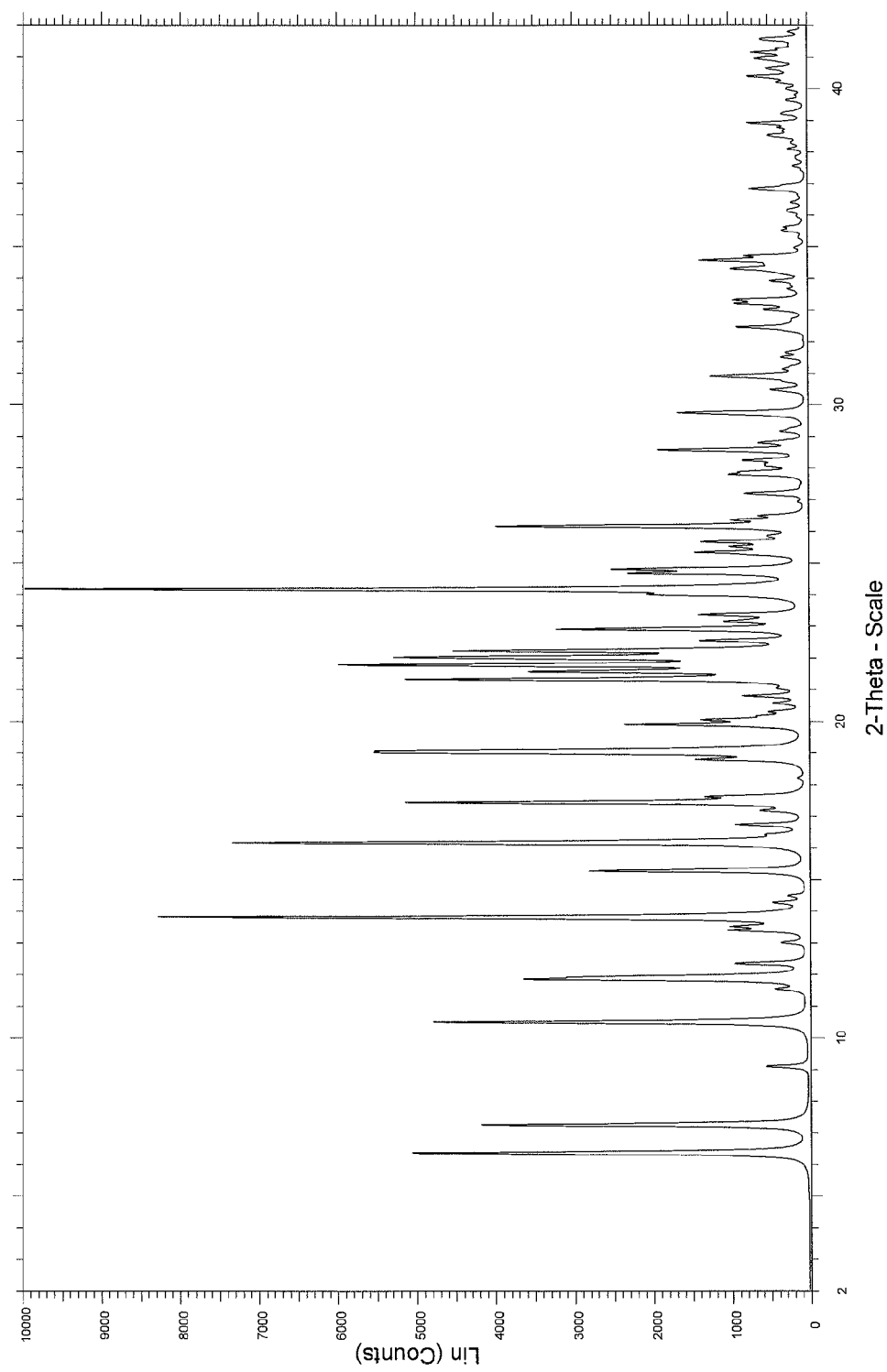
FIG. 17 shows a calculated XRPD pattern for the 1:1:1 aprepitant L-proline n-PrOH cocrystal at 100 K.

The calculated XRPD pattern based on the single crystal data and structure for the 1:1:1 aprepitant L-proline $H_2O$ cocrystal at 100 K is shown in FIG. 17.

TABLE 6

| | |
|---|---|
| Molecular formula | $C_{31}H_{38}N_5O_6F_7$ |
| Molecular weight | 709.66 |
| Crystal System | Orthorhombic |
| Space Group | $P2_12_12_1$ |
| Unit Cell Dimensions | a = 8.8539(1) Å |
| | b = 13.6136(2) Å |
| | c = 27.8997(4) Å |
| | α = 90° |
| | β = 90° |
| | γ = 90° |
| Cell Volume | V = 3362.85(8) Å$^3$ |
| Z | 4 |
| Temperature | 100(1) K |
| Radiation Wavelength/type | 1.54178/CuKα |
| Number of Reflections collected | 17471 |
| Number of unique reflections | 6831 |
| $R_{int}$ | 0.0283 |

TABLE 6-continued

| | |
|---|---|
| Number of observed Reflections, (I > 2σ(I)) | 6524 |
| Resolution, Max. 2θ, Completeness | 0.80 Å, 149.0°, 99.3% |
| wR² (all data) | 0.1028 |
| R₁ (I > 2σ(I)) | 0.0385 |
| Goodness of Fit | 1.009 |
| Flack parameter | 0.01(9) |
| Residual density (Max. Min.), eÅ⁻³ | 0.397, −0.216 |
| Morphology | Colourless block |

Figure 18:
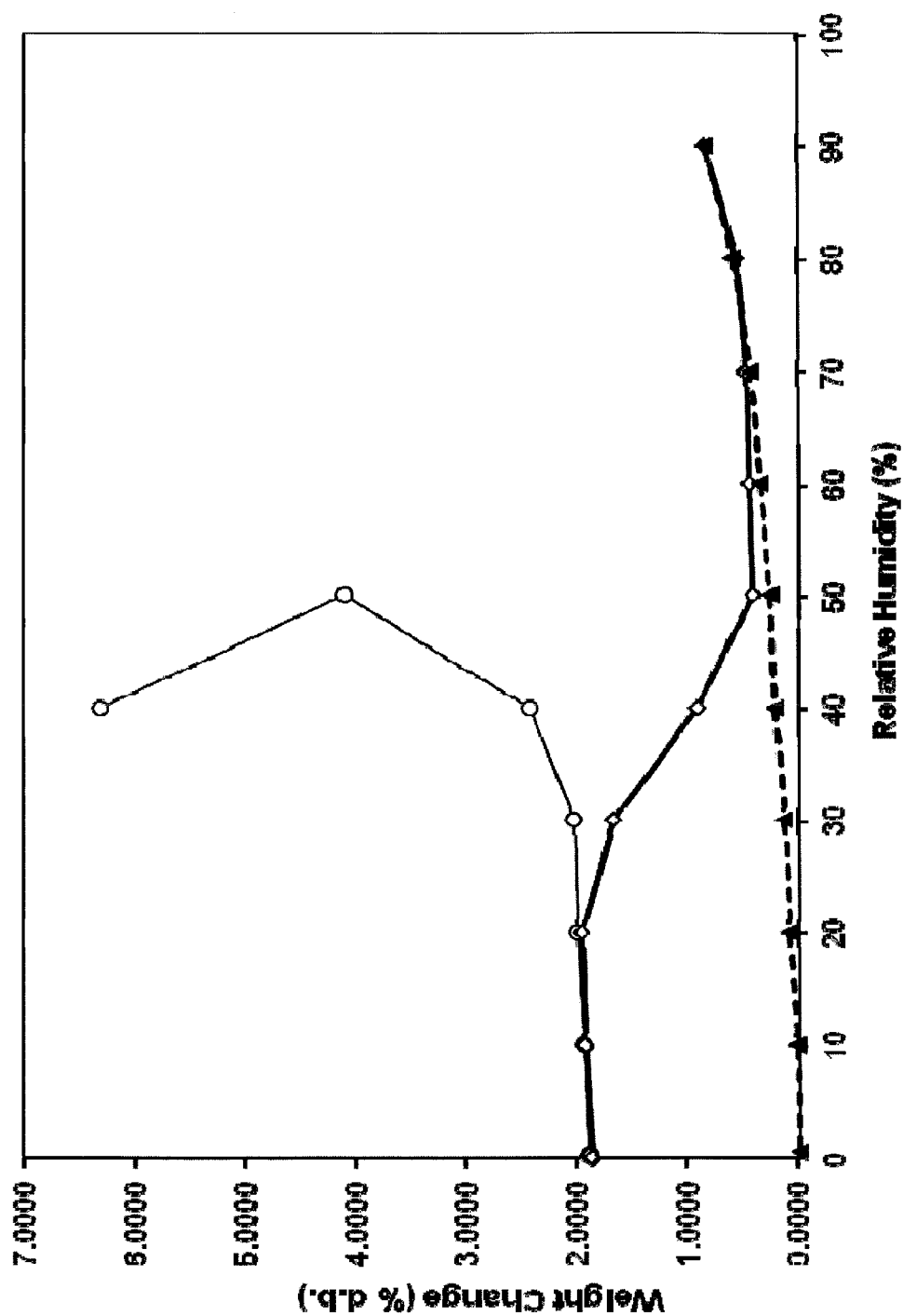
FIG. 18 shows the GVS isotherm graph for the 1:1:1 aprepitant L-proline n-PrOH cocrystal.

3.3 Gravimetric Vapour Sorption (GVS) Analysis of the 1:1:1 Aprepitant L-Proline n-PrOH Cocrystal The moisture sorption isotherm graph obtained for the 1;1:1 aprepitant L-proline n-PrOH cocrystal is shown in FIG. 18. A sample sire of 12.0 mg was used for the analysis. It can be seen that during the initial desorption cycle a weight loss of 4.4% occurs. Over the total desorption-adsorption-desorption cycles a weight loss of 6.3% occurs. XRPD analysis of the product obtained after the GVS analysis confirmed that this was entirely the 1:1:1 aprepitant L-proline H₂O cocrystal. A weight loss of 6.3% corresponds to the conversion of the 1:1:1 aprepitant L-proline n-PrOH cocrystal into the 1:1:1 aprepitant L-proline H₂O cocrystal.

The claimed invention is:

1. An aprepitant L-proline solvate composition selected from a 1:1:1 aprepitant L-proline methanol composition, a 1:1:1 aprepitant L-proline ethanol composition, and a 1:1:1 aprepitant L-proline n-propanol composition.

2. An aprepitant L-proline solvate composition selected from a 1:1:1 aprepitant L-proline methanol cocrystal, a 1:1:1 aprepitant L-proline ethanol cocrystal, and a 1:1:1 aprepitant L-proline n-propanol cocrystal.

3. A pharmaceutical composition comprising an aprepitant L-proline composition of claim 1 and a pharmaceutically acceptable carrier.

4. A method of treating disorders relating to emesis comprising the step of administering to a patient in need thereof a therapeutically effective amount of an aprepitant L-proline composition of claim 1.

5. A method of treating disorders relating to emesis comprising the step of administering to a patient in need thereof a therapeutically effective amount of a pharmaceutical composition of claim 3.

6. A 1:1:1 aprepitant L-proline methanol cocrystal characterised by at least one of:
   a powder x-ray diffraction pattern having at least three peaks selected from the peaks at 7.1, 9.1, 10.5, 16.4, 21.6 and 21.9°2θ±0.2°2θ; and
   a powder x-ray diffraction pattern substantially similar to FIG. 1; and
   a P2₁2₁2₁ space group at 100K.

7. A pharmaceutical composition comprising a 1:1:1 aprepitant L-proline methanol cocrystal of claim 6 and a pharmaceutically acceptable carrier.

8. A method of treating disorders relating to emesis comprising the step of administering to a patient in need thereof a therapeutically effective amount of a 1:1:1 aprepitant L-proline methanol cocrystal of claim 6.

9. A 1:1:1 aprepitant L-proline ethanol cocrystal characterised by at least one of:
   a powder x-ray diffraction pattern having at least three peaks selected from the peaks at 7.2, 9.1, 10.4, 16.2, 21.6 and 22.0°2θ±0.2°2θ;
   a powder x-ray diffraction pattern substantially similar to FIG. 9; and
   a P2₁2₁2₁ space group at 100K.

10. A pharmaceutical composition comprising a 1:1:1 aprepitant L-proline ethanol cocrystal of claim 9 and a pharmaceutically acceptable carrier.

11. A method of treating disorders relating to emesis comprising the step of administering to a patient in need thereof a therapeutically effective amount of a 1:1:1 aprepitant L-proline ethanol cocrystal of claim 9.

12. A 1:1:1 aprepitant L-proline n-propanol cocrystal characterised by at least one of:
   a powder x-ray diffraction pattern having at least three peaks selected from the peaks at 6.3, 7.1, 9.0, 10.4, 13.7 and 17.3°2θ±0.2°2θ;
   a powder x-ray diffraction pattern substantially similar to FIG. 14; and
   a P2₁2₁2₁ space group at 100K.

13. A pharmaceutical composition comprising a 1:1:1 aprepitant L-proline n-propanol cocrystal of claim 12 and a pharmaceutically acceptable carrier.

14. A method of treating disorders relating to emesis comprising the step of administering to a patient in need thereof a therapeutically effective amount of a 1:1:1 aprepitant L-proline n-propanol cocrystal of claim 12.

15. A pharmaceutical composition comprising an aprepitant L-proline cocrystal of claim 2 and a pharmaceutically acceptable carrier.

16. A method of treating disorders relating to emesis comprising the step of administering to a patient in need thereof a therapeutically effective amount of an aprepitant L-proline cocrystal of claim 2.

17. A method of treating disorders relating to emesis comprising the step of administering to a patient in need thereof a therapeutically effective amount of a pharmaceutical composition of claim 15.

18. A method of treating disorders relating to emesis comprising the step of administering to a patient in need thereof a therapeutically effective amount of a pharmaceutical composition of claim 7.

19. A method of treating disorders relating to emesis comprising the step of administering to a patient in need thereof a therapeutically effective amount of a pharmaceutical composition of claim 10.

20. A method of treating disorders relating to emesis comprising the step of administering to a patient in need thereof a therapeutically effective amount of a pharmaceutical composition of claim 13.

* * * * *